United States Patent [19]
Kogan et al.

[11] Patent Number: 5,444,050
[45] Date of Patent: Aug. 22, 1995

[54] BINDING OF E-SELECTIN OR P-SELECTIN TO SIALYL LEWIS$^x$ OR SIALYL-LEWIS$^a$

[75] Inventors: Timothy P. Kogan, Sugar Land; Brian Dupré, Houston; Ian L. Scott, Houston; Karin Keller, Houston; Huong Dao, Houston; Pamela J. Beck, Houston, all of Tex.

[73] Assignee: Texas Biotechnology Corporation, Houston, Tex.

[21] Appl. No.: 235,293

[22] Filed: Apr. 29, 1994

[51] Int. Cl.$^6$ .................. A61K 31/70; C07H 15/20
[52] U.S. Cl. ..................... 514/25; 536/17.2; 536/17.3; 536/17.4; 536/17.5; 536/18.4
[58] Field of Search ............ 514/25; 536/17.2, 17.3, 536/18.4, 17.4, 17.5

[56] References Cited
U.S. PATENT DOCUMENTS

| | | | |
|---|---|---|---|
| 5,212,298 | 5/1993 | Rademacher et al. | 536/55.2 |
| 5,268,364 | 12/1993 | Kojima et al. | 514/25 |
| 5,280,113 | 1/1994 | Rademacher et al. | 536/55.2 |
| 5,304,640 | 4/1994 | Lasky et al. | 536/23.5 |
| 5,318,890 | 6/1994 | Rosen et al. | 435/7.24 |

OTHER PUBLICATIONS

Yokoyama et al. Chem. Abstr. 119:256293, JP05201846, Aug. 10, 1993.
Kato et al. Chem. Abstr. 119: 233702, JP04261115, Sep. 17, 1992.
Kato et al, Chem. Abstr. 118: 66609, JP04270298, Sep. 25, 1992.
Yokota et al. Chem Abstr. 119: 188294, JP05163115, Jun. 29, 1993.
Yokota et al. Chem. Abstr. 119: 55727, JP05078230, Mar. 30, 1993.
Istudor et al. Farmacia (Bucharest) 1984, 32(3), 173–82, Chem. Abstr. 102:50763.
El–Dakhakny et al. J. Pharm Sci. 1970, 59(4), 551–553.
Winter et al. J. Chromatogr. 1984, 315, 243–251.
Luyengi et al. J. Nat. Prod. 1993, 56(11), 2012–2015.
Dahmen et al. Acta Chem. Scand. B 1975, 29, 627–639.

Primary Examiner—Douglas W. Robinson
Assistant Examiner—Kathleen Kahler Fonda
Attorney, Agent, or Firm—Dressler, Goldsmith, Shore & Milnamow, Ltd.

[57] ABSTRACT

This invention relates to compounds that inhibit the binding of E-selectin and/or P-selectin to sialyl-Lewis$^x$ or sialyl-Lewis$^a$ presented on a cell surface having the general structure

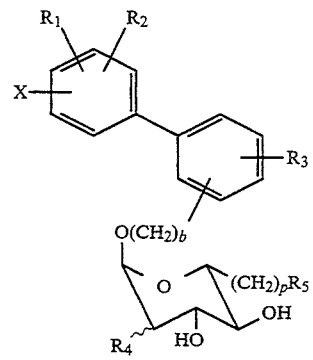

wherein X is selected from the group consisting of
—$(CH_2)_nCO_2H$, —$O(CH_2)_mCO_2H$, —$(CH_2)_nO(CH_2)_mCO_2H$, —$CONH(CH_2)_mCO_2H$, —$CH(OZ)(CO_2H)$, —$CH(Z)(CO_2H)$, —$(CH_2)_nSO_3H$, —$(CH_2)_nPO_3D_1D_2$, —$NH(CH_2)_mCO_2H$, —$CONH(CHR_6)CO_2H$, (1-H-tetrazolyl-5-alkyl-), and —OH;

$R_1$ and $R_2$ are independently selected from the group consisting of hydrogen, alkyl, halogen, —OZ, —$NO_2$, —$NH_2$ and —NHZ;

$R_3$ is selected from the group consisting of hydrogen, halogen, alkyl, —OZ and —NHZ;

$R_4$ is selected from the group consisting of hydrogen, halogen, alkyl, hydroxyl, hydroxyl-O-sulfate and —OZ;

$R_5$ is selected from the group consisting of hydroxyl, —CN, —$N_3$, —$NH_2$, —$NHNH_2$, —$NE_1E_2$, —$NHE_1$, —$NHCO(CH_2)_nCO_2H$, —$S(CH_2)_mCO_2H$ and —$NHCHNHNH_2$;

$R_6$ is selected from the group consisting of hydrogen, (Abstract continued on next page.)

alkyl, aralkyl, hydroxyalkyl, aminoalkyl, alkyl carboxylic acid and alkyl carboxamide;

wherein n is 0 to 6, m is 1 to 6, p is 0 to 6, b is 0 to 2, Z is alkyl, aryl or aralkyl, $D_1$ and $D_2$ are independantly hydrogen or alkyl, $E_1$ is alkyl or $-(CH_2)_8CO_2H$, and $E_2$ is alkyl, and the pharmaceutically acceptable salts, esters, amides, and prodrugs thereof. This invention also relates to methods of inhibiting the binding of E-selectin and/or P-selectin to sialyl-Lewis$^x$ or sialyl-Lewis$^a$ presented on a cell surface using said compounds and to pharmaceutically active compositions comprising compounds that inhibit the binding of E-selectin to sialyl-Lewis$^x$ and to methods of treatment of septic shock, ARDS, Crohn's disease, chronic inflammatory diseases, such as psoriasis and rheumatoid arthritis, and reperfusion injuries that occur following heart attacks, strokes and organ transplants.

19 Claims, No Drawings

BINDING OF E-SELECTIN OR P-SELECTIN TO SIALYL LEWIS$^x$ OR SIALYL-LEWIS$^a$

TECHNICAL FIELD

This invention relates to compounds that inhibit the binding of E-selectin or P-selectin to sialyl-Lewis$^x$ and sialyl-Lewis$^a$ and to methods of inhibiting the binding of E-selectin or P-selectin to sialyl-Lewis$^x$ or sialyl-Lewis$^a$ using said compounds. This invention also relates to pharmaceutically active compositions comprising compounds that inhibit the binding of E or P-selectin to sialyl-Lewis$^x$ or sialyl-Lewis$^a$.

BACKGROUND OF THE INVENTION

E-selectin, which has also been called ELAM-1 for endothelial leukocyte adhesion molecule-1 and LECAM-2 for lectin cell adhesion molecule, is a glycoprotein that is found on the surface of endothelial cells, the cells that line the interior wall of capillaries. E-selectin recognizes and binds to the carbohydrate sialyl-Lewis$^x$ (sLe$^x$), which is present on the surface of certain white blood cells. E-selectin helps white blood cells recognize and adhere to the capillary wall in areas where the tissue surrounding the capillary has been infected or damaged. E-selectin is actually one of three selectins now known. The other two are L-selectin and P-selectin. P-selectin is expressed on inflamed endothelium and platelets, and has much structural similarity to E-selectin and can also recognize sialyl-Lewis$^x$. The structure of sialyl-Lewis$^x$ and sialyl-Lewis$^a$ (sLe$^a$) are shown in formulas I$_a$ and I$_b$ below:

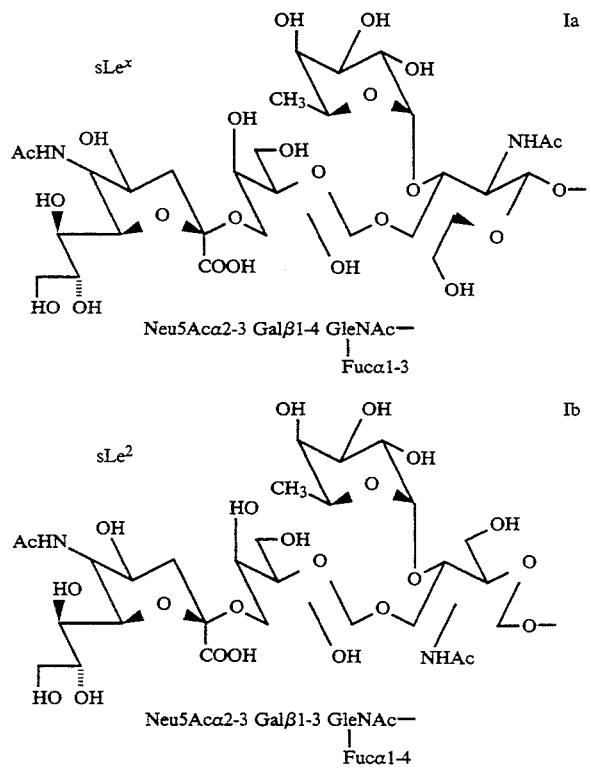

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells must be able to recognize the invaded or damaged tissue and be able to bind to the wall of the capillary near the affected tissue and diffuse through the capillary into the affected tissue. E-selectin helps two particular types of white blood cells recognize the affected sites and bind to the capillary wall so that these white blood cells may diffuse into the affected tissue.

There are three main types of white blood cells: granulocytes, monocytes and lymphocytes. Of these categories, E-selectin recognizes sLe$^x$ presented as a glycoprotein or glycolipid on the surface of monocytes and neutrophils. Neutrophils are a subclass of granulocytes that phagocytose and destroy small organisms, especially bacteria. Monocytes, after leaving the bloodstream through the wall of a capillary, mature into macrophages that phagocytose and digest invading microorganisms, foreign bodies and senescent cells.

Monocytes and neutrophils are able to recognize the site where tissue has been damaged by binding to E-selectin, which is produced on the surface of the endothelial cells lining capillaries when the tissue surrounding a capillary has been infected or damaged. Typically, the production of E-selectins and P-selectins are increased when the tissue adjacent a capillary is affected. P-selectin is present constitutively in storage granules from which it can be rapidly mobilized to the cell surface after the endothelium has been activated. In contrast, E-selectin requires de novo RNA and protein synthesis, and peak expression does not occur until about 4–6 hours after activation, and declines to basal levels after about 24–48 hours. White blood cells recognize affected areas because sLe$^x$ moieties present on the surface of the white blood cells bind to E-selectin and P-selectin. This binding slows the flow of white blood cells through the bloodstream, since it mediates the rolling of leukocytes along the activated endothelium prior to integrin mediated attachment and migration, and helps to localize white blood cells in areas of injury or infection.

While white blood cell migration to the site of injury helps fight infection and destroy foreign material, in many instances this migration can get out of control, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to E-selectin or P-selectin. For example, some of the diseases that might be treated by the inhibition of selectin binding to sLe$^x$ include, but are not limited to, ARDS, Crohn's disease, septic shock, traumatic shock, multi-organ failure, autoimmune diseases, asthma, inflammatory bowel disease, psoriasis, rheumatoid arthritis and reperfusion injury that occurs following heart attacks, strokes and organ transplants. In addition to being found on some white blood cells, sLe$^a$, a closely related regiochemical isomer of sLe$^x$, is found on various cancer cells, including lung and colon cancer cells. It has been suggested that cell adhesion involving sLe$^x$ may be involved in the metastasis of certain cancers.

SUMMARY OF THE INVENTION

The present invention provides compounds having the structure of formula II below:

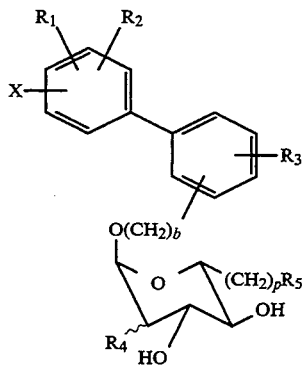

wherein X is selected from the group consisting of —$(CH_2)_nCO_2H$, —$O(CH_2)_mCO_2H$, —$(CH_2)_nO(CH_2)_mCO_2H$, —$CONH(CH_2)_mCO_2H$, —$CH(OZ)(CO_2H)$, —$CH(Z)(CO_2H)$, —$(CH_2)_nSO_2H$, —$(CH_2)_nPO_3D_1D_2$, —$NH(CH_2)_mCO_2H$, —$CONH(CHR_6)CO_2H$, (1-H-tetrazolyl-5-alkyl-), and —OH;

$R_1$ and $R_2$ are independently selected from the group consisting of hydrogen, alkyl, halogen, —OZ, —$NO_2$, —$NH_2$ and —NHZ;

$R_3$ is selected from the group consisting of hydrogen, halogen, alkyl, —OZ and —NHZ;

$R_4$ is selected from the group consisting of hydrogen, halogen, alkyl, hydroxyl, hydroxyl-O-sulfate and —OZ;

$R_5$ is selected from the group consisting of hydroxyl, —CN, —$N_3$, —$NH_2$, —$NHNH_2$, —$NE_1E_2$, —$NHE_1$, —$NHCO(CH_2)_nCO_2H$, —$S(CH_2)_mCO_2H$ and —$NHCHNHNH_2$; and $R_6$ is selected from the group consisting of hydrogen, alkyl, aralkyl, hydroxyalkyl, aminoalkyl, alkyl carboxylic acid and alkyl carboxamide;

wherein n is 0 to 6, m is 1 to 6, p is 0 to 6, b is 0 to 2, Z is alkyl, aryl or aralkyl, $D_1$ and $D_2$ are independently hydrogen or alkyl, $E_1$ is alkyl or —$(CH_2)_aCO_2H$ wherein $a$ is 1 to 18, and $E_2$ is alkyl, and the pharmaceutically acceptable salts, esters, amides and prodrugs thereof.

More particularly, this invention provides compounds of the formula III:

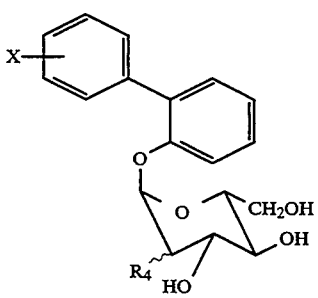

wherein X is —Q, —$(CH_2)_nQ$, —$O(CH_2)_nQ$, —$(CH_2)_nO(CH_2)_mQ$, —$CONH(CH_2)_nQ$, —$NH(CH_2)_mQ$, —$O(CH_2)_nO(CH_2)_mQ$, or —$CONH(CHR_6)Q$;

$R_4$ is hydroxyl or hydrogen; $R_6$ is selected from the group consisting of hydrogen, alkyl, aralkyl, hydroxyalkyl, aminoalkyl, alkyl carboxylate, and alkyl carboxamide; Q is —$CO_2H$, n is 0 to 6, and m is 1 to 6, and the pharmaceutically acceptable salts, esters, amides and prodrugs thereof.

The present invention also provides a method of inhibiting the binding of E-selectin or P-selectin to sLe$^x$ or sLe$^a$ comprising the step of administering to a patient an effective amount of a compound having the structure of formula II or III to inhibit the binding of E-selectin or P-selectin to sLe$^x$ or sLe$^a$, and a pharmaceutically active composition comprising a compound of formula II or III and a pharmaceutically acceptable carrier.

Also provided is a method for treating diseases such as ARDS, Crohn's disease, septic shock, traumatic shock, multi-organ failure, autoimmune diseases, asthma, inflammatory bowel disease, psoriasis, rheumatoid arthritis, reperfusion injury that occurs following heart attacks, and strokes and organ transplants which comprises administering to an animal in need of such treatment a therapeutically effective amount of a compound having the formula II or III to reduce the symptoms of the disease.

DETAILED DESCRIPTION OF THE PREFERRED EMBODIMENTS

It has been found that compounds having the formula (II) shown below act to inhibit E-selectin or P-selectin binding to sLe$^x$ or sLe$^a$:

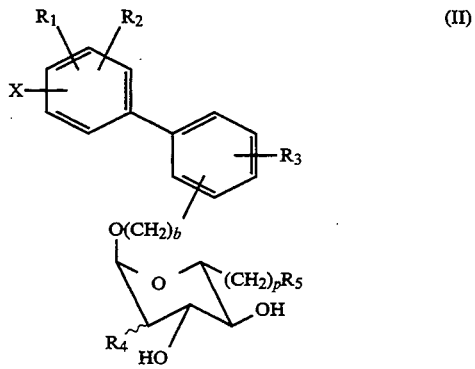

wherein X is selected from the group consisting of —$(CH_2)_nCO_2H$, $O(CH_2)_mCO_2H$, —$(CH_2)_nO(CH_2)_mCO_2H$, —$CONH(CH_2)_mCO_nH$, —$CH(OZ)(CO_2H)$, —$CH(Z)(CO_2H)$, —$(CH_2)_nSO_3H$, —$(CH_2)_nPO_3D_1D_2$, —$NH(CH_2)_mCO_2H$, —$CONH(CHR_6)CO_2H$, (1-H-tetrazolyl-5-alkyl-), and —OH;

$R_1$ and $R_2$ are independently selected from the group consisting of hydrogen, alkyl, halogen, —OZ, —$NO_2$, —$NH_2$ and —NHZ;

$R_3$ is selected from the group consisting of hydrogen, halogen, alkyl, —OZ and —NHZ;

$R_4$ is selected from the group consisting of hydrogen, halogen, alkyl, hydroxyl, hydroxyl-O-sulfate and —OZ;

$R_5$ is selected from the group consisting of hydroxyl, —CN, —$N_3$, —$NH_2$, —$NHNH_2$, —$NE_1E_2$, —$NHE_1$, —$NHCO(CH_2)_nCO_2H$, —$S(CH_2)_mCO_2H$ and —$NHCHNHNH_2$; and $R_6$ is selected from the group consisting of hydrogen, alkyl, aralkyl, hydroxyalkyl, aminoalkyl, alkyl carboxylic acid and alkyl carboxamide;

wherein n is 0 to 6, m is 1 to 6, p is 0 to 6, b is 0 to 2, Z is alkyl, aryl or aralkyl, $D_1$ and $D_2$, are independently hydrogen or alkyl, $E_1$ is alkyl or —(CH$_2$)$_a$CO$_2$H wherein a is 1 to 18, and $E_2$ is alkyl and the pharmaceutically acceptable salts, esters, amides and prodrugs thereof.

The compounds of formula II comprise two major components: a mannopyranoside derived moiety (a carbohydrate) and a biphenyl moiety. With respect to the mannopyranoside moiety, D-mannopyranosides are preferred over L-mannopyranosides, and the absolute stereochemistry shown in formula II at the $C_3$ and $C_4$ positions of the mannose sugar is preferred. However, epimeric stereochemistry is permitted at the $C_2$ position of the carbohydrate moiety (using glucopyranosides). The carbohydrate moiety will herein be called a mannopyranoside for the sake of simplicity. Also, the $\alpha$-anomer is preferred over the $\beta$-anomer.

The mannopyranoside moiety is attached to the biphenyl moiety via an —O—(CH$_2$)$_b$— bridge where b is 0 to 2. Preferably, the mannopyranoside is attached to the ortho or meta positions on the phenyl ring.

In addition, the mannopyranoside moiety may be substituted. Particularly preferred are mannopyranosides having substituents at the $C_2$ and $C_6$ positions. For example, the mannose 6-position may be substituted with groups such as hydroxyl, —CN, —N$_3$, —NH$_2$, —NHNH$_2$, —NE$_1$E$_2$, —NHE$_1$, —NHCO(CH$_2$)$_n$CO$_2$H, —S(CH$_2$)$_m$CO$_2$H or —NHCHNHNH$_2$ wherein n is 0 to 6, m is 1 to 6, $E_1$ is alkyl or —(CH$_2$)$_a$CO$_2$H and $E_2$ is alkyl. Similarly, the $C_2$ position may be substituted with hydrogen, halogen, alkyl, hydroxyl, hydroxyl-O-sulfate or alkoxy. It is preferred, however, that the alkyl group is a lower alkyl group. It is also recognized that the mannopyranoside moiety may have substituents at either the $C_2$ or $C_6$ positions or both.

The second component of the compounds of the present invention comprises a biphenyl moiety. The biphenyl moiety may be substituted at both phenyl groups or may be substituted at only one phenyl group. Moreover, each phenyl group may have more than one substituent.

The phenyl group that is not directly attached to the mannose moiety is substituted. Preferably, this phenyl group is substituted at the 3 or 4 position (meta or para) with one of the group consisting of —(CH$_2$)$_n$CO$_2$H, —O(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_6$)CO$_2$H, (1-H-tetrazolyl-5-alkyl-) and —OH wherein n is 0 to 6, m is 1 to 6, Z is alkyl, $D_1$ and $D_2$ are independently hydrogen or alkyl, $R_6$ is selected from the group consisting of hydrogen, alkyl, aralkyl, hydroxyalkyl, aminoalkyl, alkyl carboxylic acid and alkyl carboxamide.

If the phenyl group not directly attached to the mannopyranoside moiety is substituted with more than one substituent, then one substituent is located at the 3 or 4 position and is selected from the group consisting of —(CH$_2$)$_n$CO$_2$H, —O(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_6$)CO$_2$H, and (1-H-tetrazolyl-5-alkyl-) wherein n is 0 to 6, m is 1 to 6, Z is alkyl, $R_6$ is selected from the group consisting of hydrogen, alkyl, aralkyl, hydroxyalkyl, aminoalkyl, alkyl carboxylic acid and alkyl carboxamide, and $D_1$ and $D_2$ are independently hydrogen or alkyl. Any other substituents are selected independently from the group consisting of hydrogen, halogen, alkyl, NO$_2$, CO$_2$H and OH.

It may also be desirable to have substitution on the phenyl ring directly attached to the mannopyranoside moiety. Substituents may be selected from the group consisting of hydrogen, halogen, alkyl, alkoxy, and alkylamino.

The most preferred compounds of the present invention have the formula III shown below:

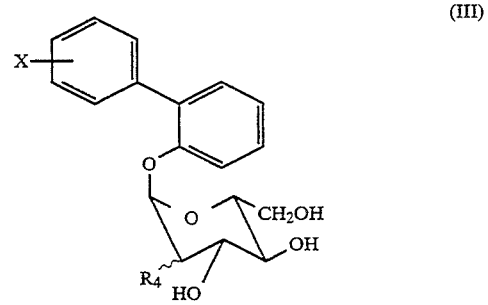

(III)

wherein X is —Q, —(CH$_2$)$_n$Q, —O(CH$_2$)$_n$Q, —(CH$_2$)$_n$O(CH$_2$)$_m$Q, —O(CH$_2$)$_n$O(CH$_2$)$_m$Q, —CONH(CH$_2$)$_n$Q, —NH(CH$_2$)$_m$Q, or —CONH(CHR$_6$)Q; $R_4$ is hydroxyl or hydrogen, $R_6$ is selected from the group consisting of hydrogen, alkyl, aralkyl, hydroxyalkyl, aminoalkyl, alkyl carboxylic acid and alkyl carboxamide, Q is —CO$_2$H, n is 0 to 6, and m is 1 to 6, and the pharmaceutically acceptable salts, esters, amides and prodrugs thereof.

As used herein, the term "alkyl" shall mean a monovalent straight chain or branched chain group of 1 to 12 carbon atoms including, but not limited to, methyl, ethyl, n-propyl,-isopropyl, n-butyl, sec-butyl, isobutyl, tert-butyl and the like.

The term "lower alkyl" shall mean any alkyl group having from one to six carbon atoms.

The term "halogen" shall mean any atom selected from the group consisting of chlorine, fluorine, bromine, and iodine.

The term "alkoxy" shall mean an alkyl group attached to a molecule through an oxygen atom including, but not limited to, methoxy, ethoxy, isopropoxy, n-butoxy, sec-butoxy, isobutoxy, tert-butoxy and the like.

The term "alkylamino" shall mean groups having the structure —NH-(alkyl), or —N-(alkyl)$_2$, including, for example, methylamino, ethylamino, isopropylamino and the like.

The term "aryl" shall mean carbocyclic aromatic groups including, but not limited to, phenyl, 1 or 2-naphthyl, fluorenyl, (1,2)-dihydronaphthyl, indenyl, indanyl, thienyl and the like.

The term "aralkyl" (also called arylalkyl) shall mean an aryl group appended to an alkyl group including, but not limited to, benzyl, 1 and 2-naphthylmethyl, halobenzyl, alkoxybenyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "hydroxyalkyl" shall mean —OH appended to an alkyl group.

The term "aminoalkyl" shall mean a group having the structure —NR$_x$R$_y$ appended to an alkyl group. The groups $R_x$ and $R_y$ are independently selected from, for example, hydrogen, alkyl and aryl.

The term "alkyl carboxylic acid shall mean a carboxyl group ($-CO_2H$) appended to an alkyl group.

The term "alkyl carboxamide" shall mean a group having the formula $-CONR_xR_y$ appended to an alkyl group where $R_x$ and $R_y$ are as defined above under aminoalkyl.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of the compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine, and the like. (See, for example S. M. Berge, et al., "Pharmaceutical Salts," *J. Pharm. Sci.*, 66: 1-19 (1977), which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well arylalkyl esters such as, but not limited to, benzyl. $C_1$ to $C_4$ alkyl esters are preferred. Esters of the compounds of the present invention may be prepared according to conventional methods.

Examples of pharmaceutically acceptable, non-toxic amides of compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the from of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield to the parent compound of the above formula, for example by hydrolysis in blood. A thorough discussion is provided in T. Higuchi and V. Stella, "Pro-drugs as Novel Delivery Systems", Vol 14 of the A. C. S. Symposium Series, and in *Bioreversible Carriers in Drug Design*, ed. Edward B. Roche, American Pharmaceutical Association and Pergamon Press, 1987, both of which are incorporated herein by reference.

The present invention also provides for pharmaceutically active compositions that contain the compounds of the present invention. It is also contemplated that pharmaceutically active compositions may contain a compound of the present invention and other compounds that inhibit or compete with E-selectin or P-selectin binding to $sLe^x$ or $sLe^a$, including $sLe^x$ and $sLe^a$ themself.

Pharmaceutically active compositions of the present invention comprise a physiological carrier and a compound of the formula:

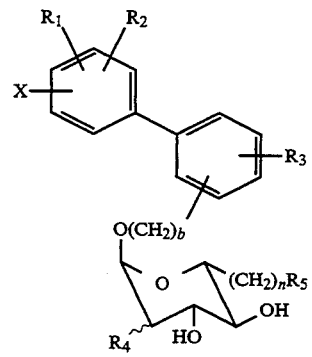

wherein X is selected from the group consisting of
$-(CH_2)_nCO_2H$, $-O(CH_2)_mCO_2H$, $-(CH_2)_nO(CH_2)_mCO_2H$, $-CONH(CH_2)_mCO_2H$, $-CH(OZ)(CO_2H)$, $-CH(Z)(CO_2H)$, $-(CH_2)_nSO_3H$, $-(CH_2)_nPO_3D_1D_2$, $-NH(CH_2)_mCO_2H$, $-CONH(CHR_6)CO_2H$, (1-H-tetrazolyl-5-alkyl-), and $-OH$;

$R_1$ and $R_2$ are independently selected from the group consisting of hydrogen, alkyl, halogen, $-OZ$, $-NO_2$, $-NH_2$ and $-NHZ$;

$R_3$ is selected from the group consisting of hydrogen, halogen, alkyl, $-OZ$ and $-NHZ$;

$R_4$ is selected from the group consisting of hydrogen, halogen, alkyl, hydroxyl, hydroxyl-O-sulfate and $-OZ$;

$R_5$ is selected from the group consisting of hydroxyl, $-CN$, $-N_3$, $-NH_2$, $-NHNH_2$, $-NE_1E_2$, $-NHE_1$, $-NHCO(CH_2)_nCO_2H$, $-S(CH_2)_mCO_2H$ and $-NHCHNHNH_2$; and $R_6$ is selected from the group consisting of hydrogen, alkyl, aralkyl, hydroxyalkyl, aminoalkyl, alkyl carboxylic acid and alkyl carboxamide;

wherein n is 0 to 6, m is 1 to 6, b is 0 to 2, Z is alkyl, aryl or aralkyl, $D_1$ and $D_2$ are independently hydrogen or alkyl, $E_1$ is alkyl or $-(CH_2)_aCO_2H$ wherein a is 1 to 18, and $E_2$ is alkyl, and the pharmaceutically acceptable salts, esters, amides and prodrugs thereof. As used herein, the term patient can include both humans and other animals.

The pharmaceutical compositions of the present invention may include one or more of the compounds having the above structures II or III formulated together with one or more nontoxic, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parentally (intravenously, intramuscularly, or subcutaneously), intracisternally, intravaginally, intraperitoneally, locally (powders, ointments or drops), or as buccal or nasal sprays.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyol,(propylene glycol, polyethylene glycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, 10 sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a pro-drug ester is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol,(d) diintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions that can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame seed oil, glycerol, tetrahydrofurfuryl alcohol, polyethylene glycols and fatty acid esters of sorbitan or mixtures of these substances, and the like.

Besides such inert diluents, the compositions can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances and the like.

Compositions for rectal administrations are preferably suppositories, which can be prepared by mixing the compounds of the present invention with suitable nonirritating excipients or carriers such as cocoa butter, polyethylene glycol or a suppository wax, which are solid at ordinary temperatures but liquid at body temperature and therefore melt in the rectal or vaginal cavity and release the active component.

Dosage forms for topical administration of a compound of this invention include ointments, powders, sprays and inhalants.

The active component is admixed under sterile conditions with a physiologically acceptable carrier and any needed preservatives, buffers or propellants as may be required. Ophthalmic formulations, eye ointments, powders and solutions are also contemplated as being within the scope of this invention.

The compounds of this invention can also be administered in the form of liposomes. As is known in the art, liposomes are generally derived from phospholipds or other lipid substances. Liposomes are formed by mono or multilamellar hydrated liquid crystals that are dispersed in an aqueous medium. Any nontoxic, physiologically acceptable and metabolizable lipid capable of forming liposomes can be used. The present compositions in liposome form can contain, in addition to the selectin binding inhibitors of the present invention, stabilizers, preservatives, excipients and the like. The preferred lipids are the phospholipids and the phosphatidyl cholines (lecithins), both natural and synthetic. Methods to form liposomes are well known in the art.

Actual dosage levels of active ingredient in the compositions of the present invention may be varied so as to obtain an amount of active ingredient that is effective to obtain the desired therapeutic response for a particular composition and method of administration. The selected dosage levels, therefore, depends on the desired therapeutic effect, on the route of administration, on the desired duration of treatment and other factors.

The total daily dosage of the compounds of this invention administered to a host in single or divided doses may be in the range of from about 5 mg to about 250 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex, diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administered to a patient to treat septic shock, chronic inflammatory diseases such as psoriasis and rheumatoid arthritis, and reperfusion tissue injury that occurs following heat attacks, strokes and organ transplants, traumatic shock, multi-organ failure, autoimmune diseases, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds inhibit the binding of E-selectin or P-selectin with sLe$^x$ or sLe$^a$, any disease that is related to this interaction may potentially be treated by the inhibition of this binding interaction.

In addition to being found on some white blood cells, sLe$^a$ is found on various cancer cells, including lung and colon cancer cells. It has been suggested that cell adhesion involving sLe$^a$ may be involved in the metastasis of certain cancers.

The compounds of the present invention may be synthesized according to the general synthetic scheme shown in scheme 1:

Scheme 1

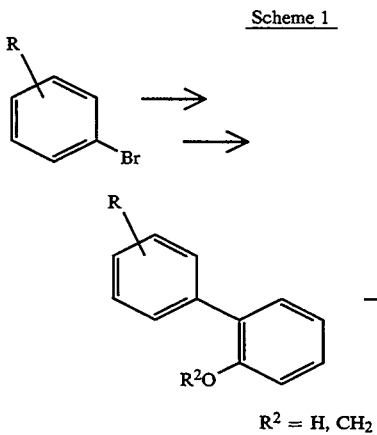

$R^2 = H, CH_2$

-continued
Scheme 1

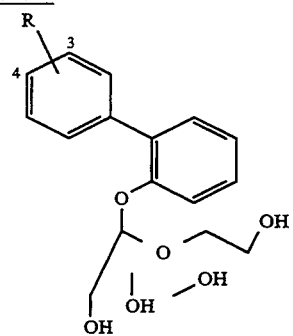

where R is selected from the group consisting of —(CH$_2$)$_n$CO$_2$H, —O(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_2$H, —(CH$_2$)$_n$PO$_3$D$_1$D$_2$, —NH(CH$_2$)$_m$CO$_2$H, —CONH(CHR$_6$)CO$_2$H, and (1 H-tetrazolyl-5-alkyl-); wherein n is 0 to 6, m is 1 to 6, Z is alkyl, D$_1$ and D$_2$ are independently hydrogen or alkyl, and R$_6$ is selected from the group consisting of hydrogen, alkyl, aralkyl, hydroxyalkyl, aminoalkyl, alkyl carboxylic acid and alkyl carboxamide, and the pharmaceutically acceptable salts, esters, amides, and prodrugs thereof.

In this scheme, the desired biphenyl moiety is synthesized and subsequently reacted with the desired mannopyranoside moiety to form a compound of the present invention. Specific examples of the synthesis of the compounds of the invention are presented in the experimental section below wherein R is as defined above.

Other compounds may be synthesized according to the schemes set forth below where R is as defined above.

Scheme 2

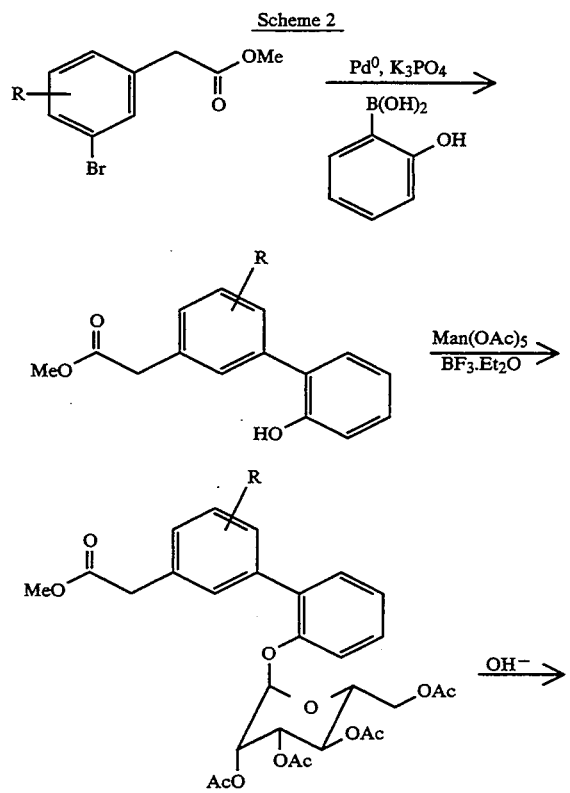

-continued
Scheme 2

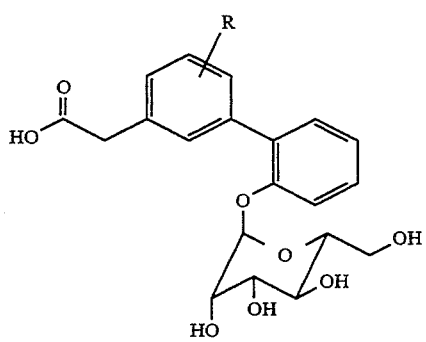

In this reaction scheme, a substituted phenylacetic ester is coupled with an aryl boronic acid in the presence of a palladium catalyst and base to give a biphenyl compound. The phenol functionality is reacted with a protected mannopyranoside in the presence of boron trifluoride etherate. The desired compound is obtained by treatment with base to hydrolyse the esters.

Scheme 3

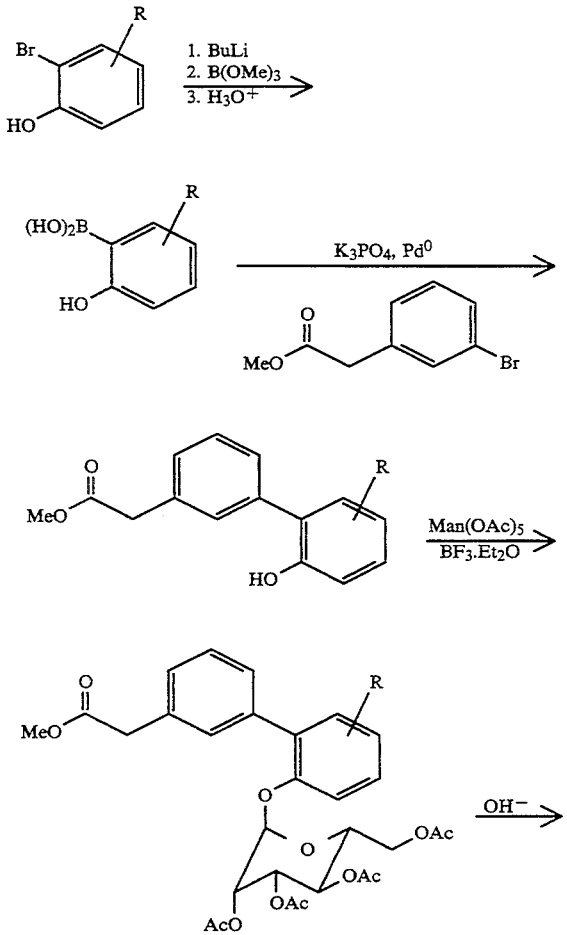

-continued
Scheme 3

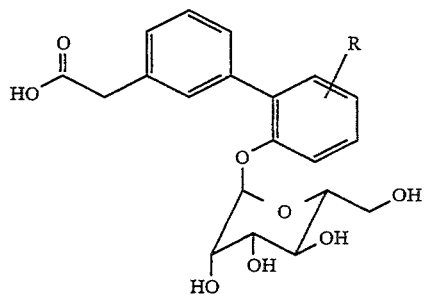

A substituted bromophenol is reacted first with butyl lithium, then with trimethoxy borate followed by acid hydrolysis to give a boronic acid. This compound is reacted with a substituted bromobenzene in a palladium(0) catalyzed coupling to give a biphenyl compound. The biphenyl compound is coupled with a protected mannopyranoside and the product is deprotected by base hydrolysis to form the desired compound.

Scheme 4

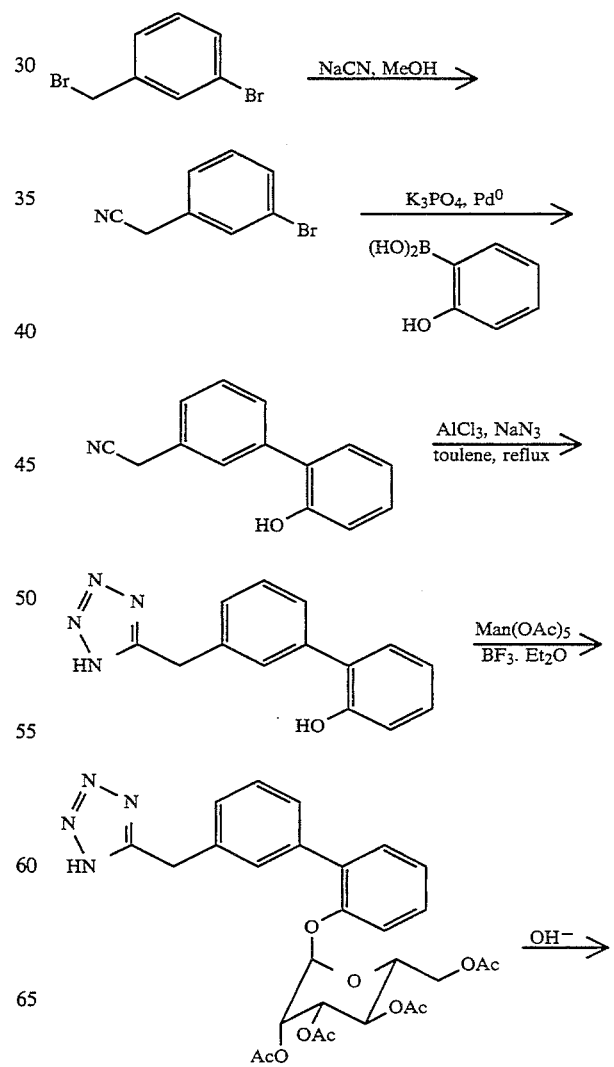

-continued
Scheme 4

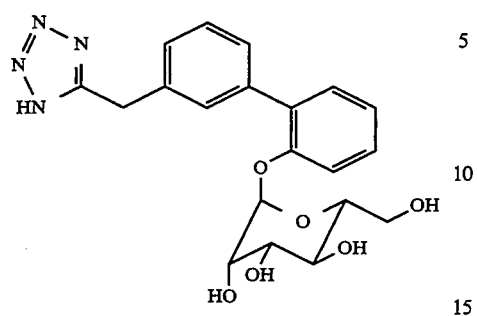

A bromobenzyl bromide is treated with sodium cyanide in refluxing methanol to give a bromobenzyl nitrile. This compound is coupled with a boronic acid in the presence of a palladium catalyst and base to give a substituted biphenyl compound. The nitrile functionality is converted to a tetrazole by treatment with sodium azide and aluminum chloride in refluxing toluene. The biphenyl tetrazole is coupled with a protected mannose derivative catalyzed by boron trifluoride etherate. Treatment with base deprotects the mannose and provides the desired compound.

-continued
Scheme 5

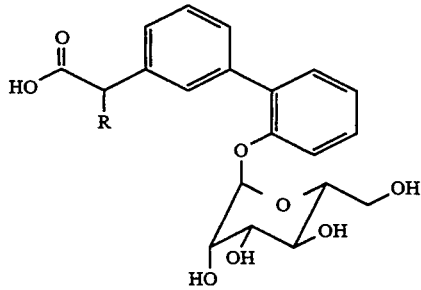

A bromophenyl acetate is treated with lithium diisopropylamide and an alkyl halide to give an α-alkyl bromophenyl acetate. This compound is coupled with a boronic acid to produce a biphenyl compound. The biphenyl compound is coupled with protected mannopyranoside using boron trifluoroetherate and the compound is deprotected by base hydrolysis to give the desired compound.

Scheme 5

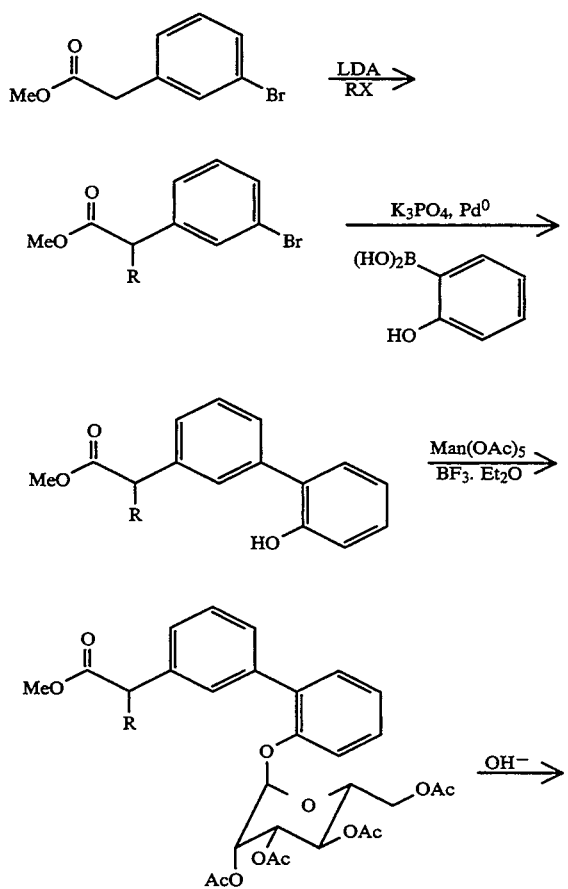

Scheme 6

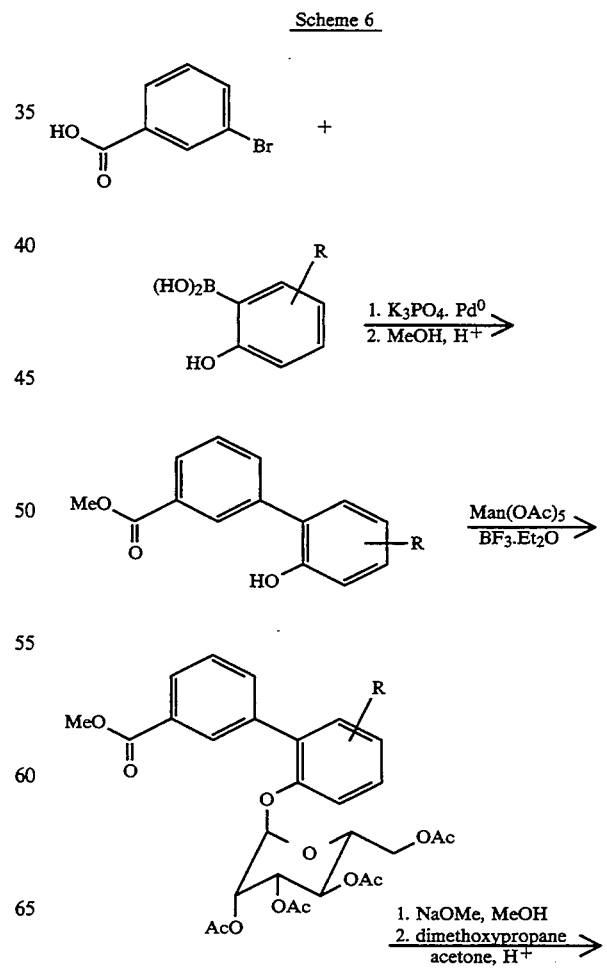

17

-continued
Scheme 6

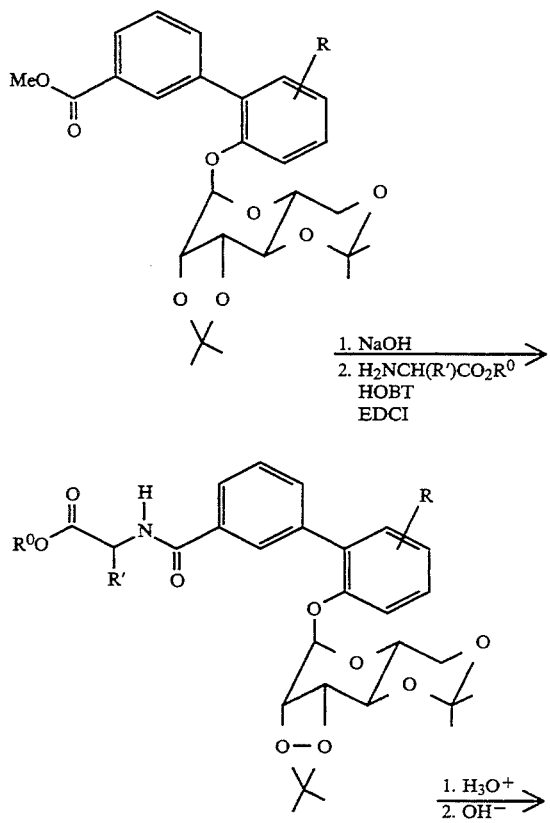

18

-continued
Scheme 6

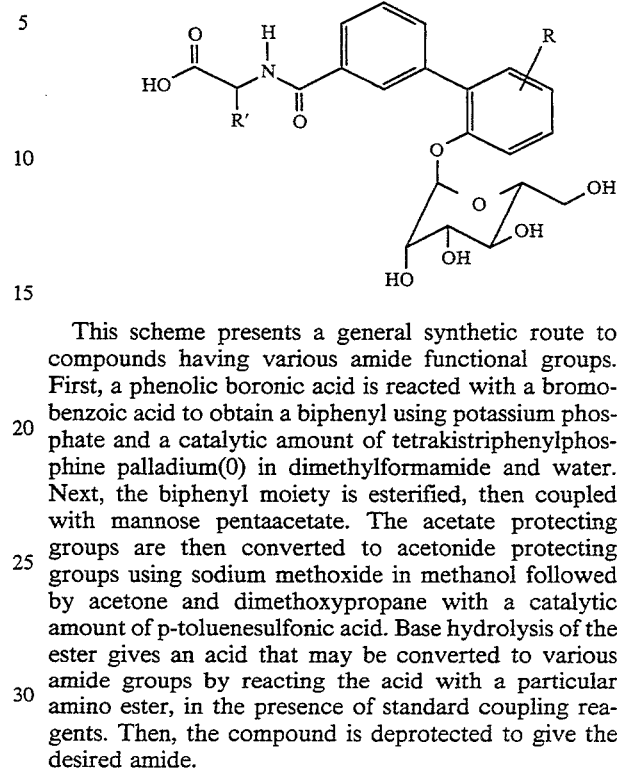

This scheme presents a general synthetic route to compounds having various amide functional groups. First, a phenolic boronic acid is reacted with a bromobenzoic acid to obtain a biphenyl using potassium phosphate and a catalytic amount of tetrakistriphenylphosphine palladium(0) in dimethylformamide and water. Next, the biphenyl moiety is esterified, then coupled with mannose pentaacetate. The acetate protecting groups are then converted to acetonide protecting groups using sodium methoxide in methanol followed by acetone and dimethoxypropane with a catalytic amount of p-toluenesulfonic acid. Base hydrolysis of the ester gives an acid that may be converted to various amide groups by reacting the acid with a particular amino ester, in the presence of standard coupling reagents. Then, the compound is deprotected to give the desired amide.

Scheme 7

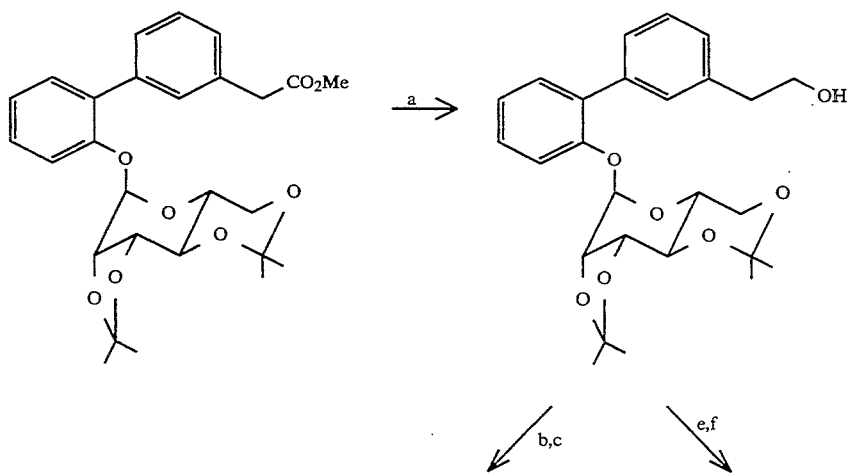

-continued
Scheme 7

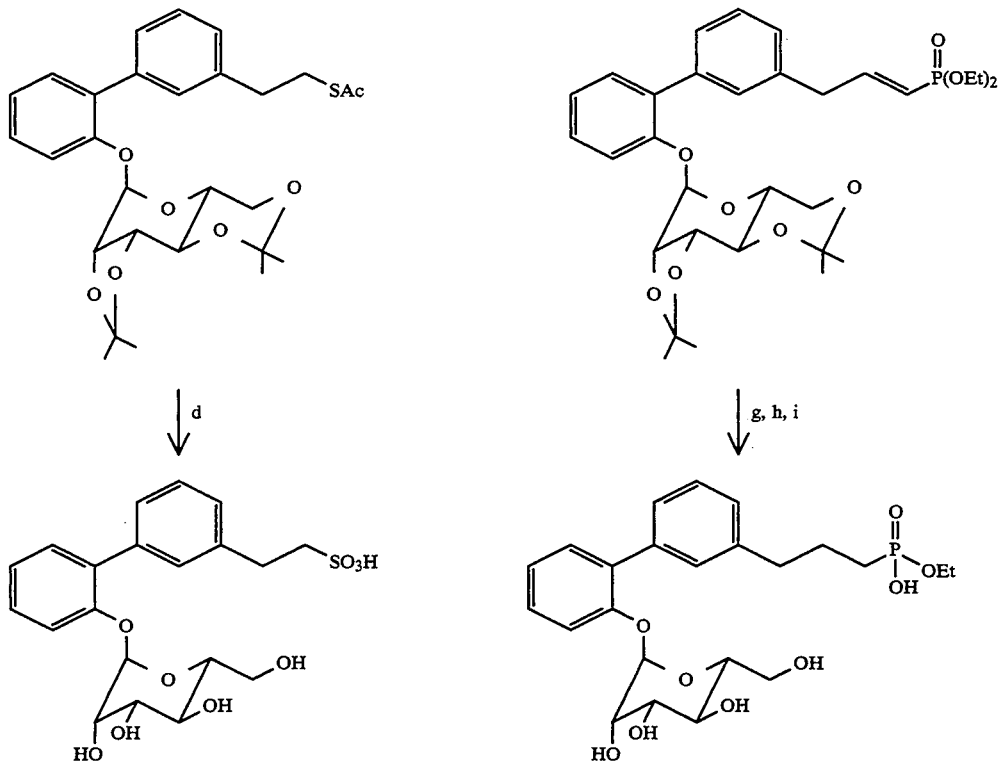

Reagents and conditions: a) LiBH$_4$, THF/toluene b) MsCl, Et$_3$N c) potassium thioacetate
d) Oxone, H$_2$O/MeOH e) Dess-Martin periodinane, CH$_2$Cl$_2$ f) KCH(PO$_3$Et$_2$)$_2$, THF g) H$_2$, Pd/C,
MeOH h) H$^+$, H$_2$O i) NaOH, H$_2$O, Δ

A compound having a biphenyl moiety and an acetonide protected mannopyranoside moiety as synthesized in scheme 6 above may be reacted with lithium borohydride in tetrahydrofuran and toluene to produce a compound having a phenylethyl alcohol group on the biphenyl moiety. This may be reacted with mesyl chloride and triethylamine followed by potassium thioacetate to give a alkyl thioacetate; this thioacetate may be further treated with Oxone in water and methanol to give a sulfonic acid substituted biphenyl compound. Alternatively, the phenylethyl alcohol may be treated with the Dess-Martin reagent to afford an aldehyde, which may then be treated with tetraethylmethylene diphosphonate anion to produce an α,β-unsaturated phosphonate. Reduction with hydrogen and a palladium catalyst produces the corresponding diethyldiphosphonate, which may then be partially hydrolyzed with aqueous base to give an ethyl phosphonic acid.

Scheme 8

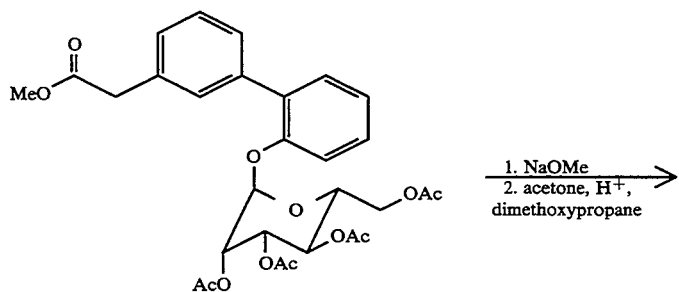

1. NaOMe
2. acetone, H$^+$, dimethoxypropane

-continued
Scheme 8
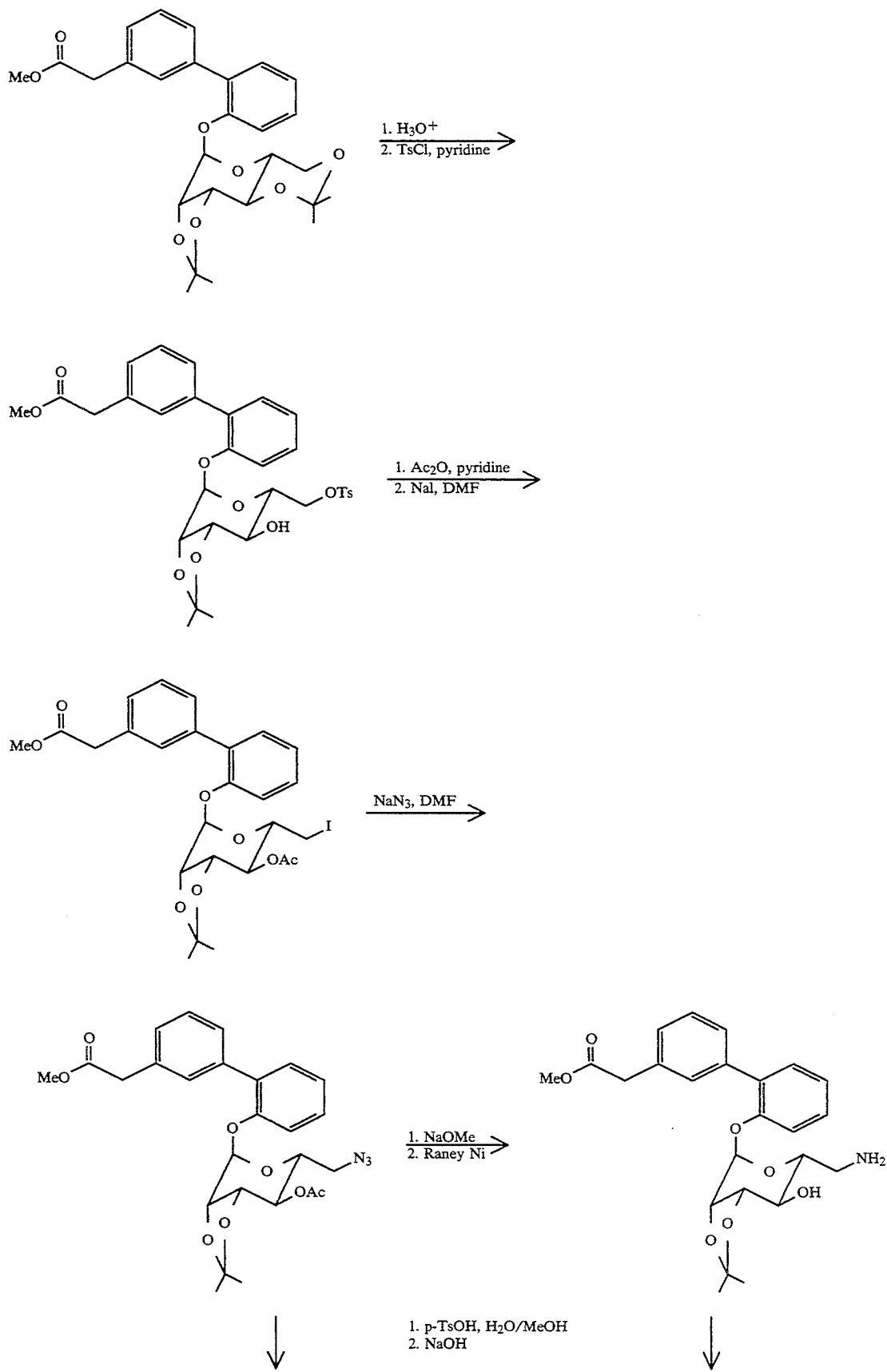

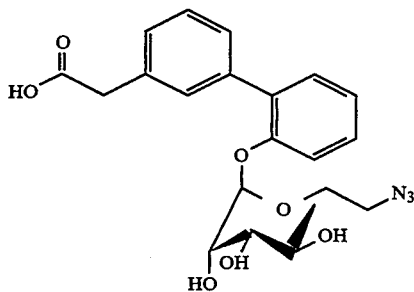

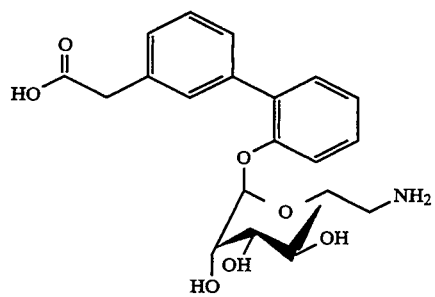

A substituted biphenyl compound having a protected mannose as prepared in Scheme 2 is treated first with sodium methoxide in methanol, then dimethoxypropane in acetone with catalytic acid to give a bisacetonide. Partial deprotection by mild acid hydrolysis, followed by reaction of the primary 6-hydroxyl group with tosyl chloride gives a hydroxy tosylate which is acetylated with acetic anhydride in pyridine. The tosylate group is replaced with an iodine using sodium iodide in dimethylformamide. Treatment of the iodide with sodium azide in DMF gives an azido compound which is either deprotected to give the 6-azido compound, or is reduced to an amine following removal of the acetate protecting group. Further removal of the remaining protecting groups by treatment with catalytic acid in methanol followed by hydrolysis gives the desired 6-amino compound.

Scheme 9

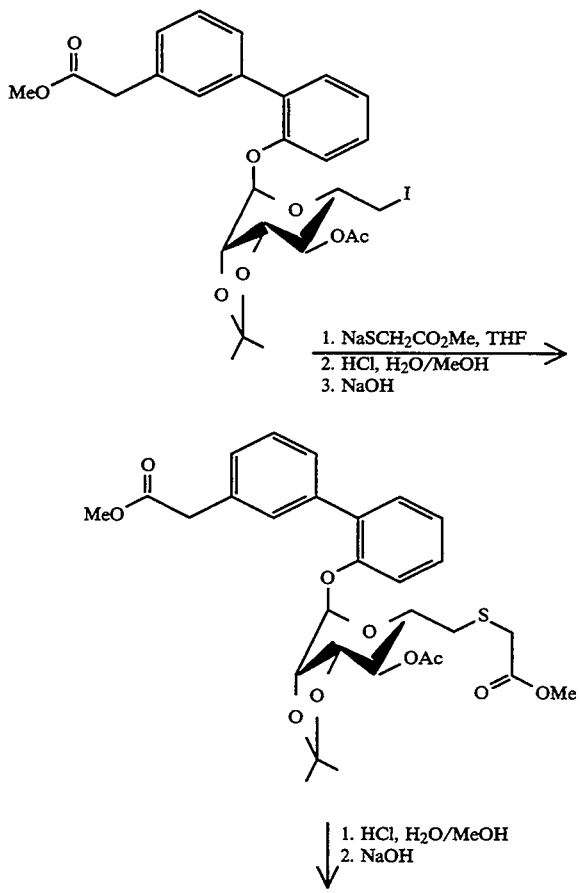

-continued
Scheme 9

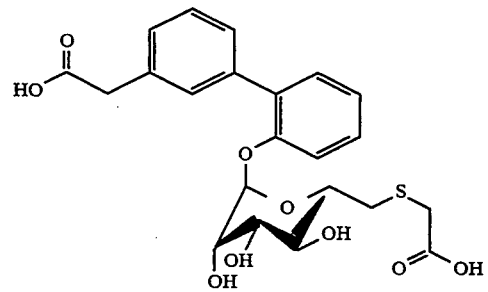

This scheme shows that the 6-iodomannopyranoside as synthesized in Scheme 8 can be displaced with a sulfur based nucleophile to generate the 6-mercapto-S-acetate ester, which can subsequently be deprotected by sequential mild acid then base hydrolysis to give the target compound.

Scheme 10

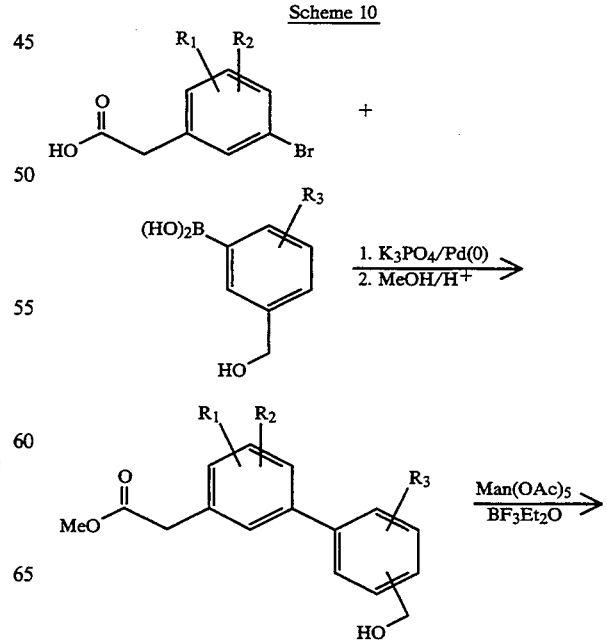

-continued
Scheme 10

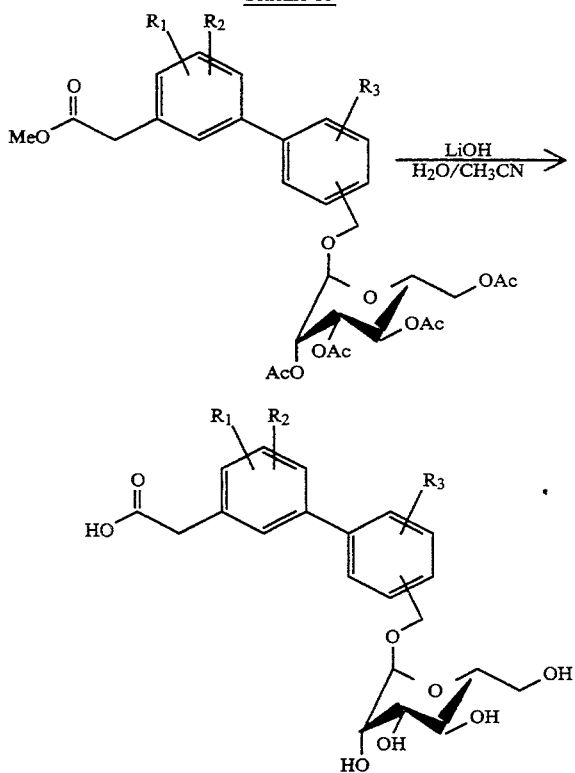

In this scheme, a substituted bromophenyl acetic acid is coupled with a substituted hydroxymethyl benzene boronic acid using a palladium (0) catalyst, and the product esterified. The resulting ester is glycosylated with a protected mannopyranoside in the presence of boron trifloride etherate. Hydrolysis of the protecting groups affords the desired compound.

The following examples further illustrate the invention and are not to be construed as limiting the specification or the claims in any way.

EXAMPLES

EXAMPLE 1

3-(3-(α-D-Mannopyranosyloxy)phenyl)phenyl acetic acid

Part A:

3-Bromophenyl acetic acid (2.0 g, 9.3 mmol) was dissolved in methanol (20 ml) in a 50 ml flask. Concentrated sulfuric acid (2 drops) was added, and the mixture was refluxed under nitrogen for ten hours then concentrated under reduced pressure. The residue was mixed with dichloromethane (20 ml) and saturated sodium bicarbonate solution (10 ml). The organic material was separated, dried (MgSO4) and concentrated under reduced pressure. The residue was flushed through silica gel with hexane/ethyl acetate (3:1), and concentrated to provide 2.12 g (99%) of methyl (3-bromophenyl)acetate, which was used without further purification.

Part B:

Anisole (2.16 g, 20.0 mmol) was dissolved in dry THF (50 ml) in a dry 100 ml flask flushed with nitrogen. The mixture was chilled in a dry ice/2-propanol bath, n-butyl lithium (10.9 ml of a 2.3M solution in hexanes, 25 mmol) was added, then the cooling bath was exchanged for an ice-water bath. The reaction was stirred for an hour at 0° C., then trimethyl borate (2.3 ml, 20 mmol) was added and the mixture was stirred at room temperature overnight. The reaction mixture was treated with 2N aqueous HCl to pH 3 and mixed well for 30 minutes, then extracted with ether (3×15 ml). The organic materials were combined, dried (MgSO4), then concentrated under reduced pressure which gave 2.88 g (95%) of 2-methoxybenzene boronic acid as a clear oil which was used in the next step without further purification.

Methyl (3-bromophenyl)acetate (2.06 g, 9.0 mmol), tetrakis(triphenylphosphine)palladium (0)(115 mg), sodium carbonate (2.61 g, 25 mmol in 2 ml water) and toluene (10 ml) were degassed under nitrogen in a 25 ml flask fitted with a reflux condenser. 2-Methoxybenzene boronic acid (1.5 g, 9.87 mmol) in toluene (1 ml) was added and the mixture was heated at reflux overnight, then mixed with 1:1 saturated sodium chloride/ethyl acetate (15 ml). The organic materials were separated, dried (MgSO4), then concentrated under reduced pressure which gave 2.81 g of methyl (3-(2-methoxyphenyl)phenyl)acetate.

Part C:

In a dry 250 ml flask, methyl 3-(2-methoxyphenyl)-phenyl acetate (2.0 g, 7.8 mmol) was dissolved in dichloromethane (100 ml) under nitrogen, and chilled in a dry-ice/2-propanol bath. Boron tribromide (2.2 ml, 24 mmol) was added slowly drop-wise and the mixture was kept at −10° C. for 14 hours, then mixed with ice-water (100 ml). The organic material was separated, washed with saturated sodium bicarbonate solution (50 ml), water (50 ml), saturated sodium chloride (60 ml), then dried (MgSO4) and concentrated under reduced pressure. The residue was purified by flash chromatography (SiO2, 3:1 hexane/ethyl acetate) which gave 1.25 g (66% from methyl (3-bromophenyl) acetate) of methyl 3-(2-hydroxyphenyl)phenyl acetate as a clear oil.

Part D:

Methyl 3-(2-hydroxyphenyl)phenyl acetate (1.28 g, 5.28 mmol) was dissolved in 1,2-dichloroethane (20 ml) in a dry 50 ml flask. Mannose pentaacetate (2.08 g, 5.34 mmol) was added in one portion, then borontrifluoride etherate (2.32 ml, 18.5 mmol) was added slowly. The mixture was stirred under nitrogen overnight at room temperature, then mixed with water (50 ml). The organic material was separated and the aqueous portion was extracted with dichloromethane (3×5 ml). The extracts were combined with the original organic fraction, dried (MgSO4), then concentrated under reduced pressure. The residue was purified by flash chromatography (SiO2, gradient elution hexane to 3:1 hexane/ethyl acetate) which provided 2.74 g (91%) of methyl 3-(2-(2,3,4,6-tetra-O-acetyl-α-D-mannopyranosyloxy)phenyl)phenyl acetate contaminated with a small amount of unreacted α-D-mannose pentaacetate which co-eluted with the product.

Part E:

Methyl 3-(2-(2,3,4,6-tetra-O-acetyl-α-D-mannopyranosyloxy)phenyl)phenyl acetate (2.74 g, 4.78 mmol) was dissolved in acetonitrile (25 ml) in a 50 ml flask, and treated with a solution of lithium hydroxide monohydrate (1.1 g, 26.3 mmol) in water (10 ml) and the mixture was stirred at room temperature overnight then acidified to pH 2 with concentrated hydrochloric acid. The mixture was concentrated under reduced pressure and the residue was purified by HPLC (reverse phase, gradient elution 5–50% acetonitrile in water (0.1% trifluoroacetic acid), monitored at 254 nm) which gave 0.87 g (47%) of 3-(2-(α-D-mannopyranosyloxy)-phenyl)phenyl acetic acid as a white solid, m.p. 85°–86° C.

$^1$H NMR: (300 MHz, DMSO-d6) 7.02–7.40 (comp,8H), 5.31 (s, 1H), 3.25–4.00 (comp, 12H) ppm.

IR (KBr): 3408, 1791, 1713, 1478, 1223, 1171, 1019, 979, 755 cm$^{-1}$.

Analysis: Calc for $C_{20}H_{22}O_8 \cdot 1.5 [H_2O]$: 57.55% C, 5.76% H.

Found 57.33% C, 5.59% H.

EXAMPLE 2

4-(2-(α-D-Mannopyranosyloxy)phenyl)phenyl acetic acid

Part A:

Operating as in Part A of EXAMPLE 1, but employing 4-bromophenyl acetic acid gave methyl 4-bromophenyl acetate in 85% yield.

Part B:

2-Bromophenol (10.0 g, 57.8 mmol) was dissolved in dry THF (100 ml) in a dry 250 ml flask flushed with nitrogen. The mixture was chilled in a dry ice/2-propanol bath, n-butyl lithium (51 ml of a 2.5M solution in hexanes, 127.2 mmol) was added, then the cooling bath was exchanged for an ice-water bath. The reaction was stirred for an hour at 0° C. then trimethyl borate (6.9 ml , 60.7 mmol) was added to the slurry which became homogeneous after a few minutes. The mixture was stirred at room temperature overnight, then treated with 2N aqueous HCl to pH 3, mixed well for 30 minutes and extracted with ether (3×25 ml). The organic materials were combined, dried (MgSO4), then concentrated under reduced pressure which gave 7.6 g (91%) of 2-hydroxybenzene boronic acid as a white solid, m.p. 156°–158° C.

Methyl (4-bromophenyl)acetate (2.79 g, 12.2 mmol), tetrakis(triphenylphosphine)palladium (0) (170 mg), potassium phosphate (9.71 g, 45.75 mmol) and dimethoxyethane (50 ml) were degassed under nitrogen in a 100 ml flask fitted with a reflux condenser. 2-Hydroxybenzene boronic acid (2.52 g, 18.3 mmol) in dimethoxyethane (5 ml) was added and the mixture was heated at reflux overnight then mixed with 1:1 saturated sodium chloride/ethyl acetate (25 ml). The organic materials were separated, dried (MgSO4), then concentrated under reduced pressure. The residue was purified by flash chromatography (SiO2, gradient hexane to 3:1 hexane/ethyl acetate) which provided 2.21 g (75%) of methyl (4-(2-hydroxyphenyl)phenyl)acetate.

Part C:

Operating as in Part D in EXAMPLE 1, but employing methyl (4-(2-hydroxyphenyl)phenyl)acetate gave methyl (4-(2-(2,3,4,6-tetra-O-acetyl-α-D-mannopyranosyloxy)phenyl)phenyl acetate in 86% yield.

Part D:

Operating as in Part E in EXAMPLE 1, but employing methyl (4-(2-(2,3,4,6-tetra-O-acetyl-α-D-mannopyranosyloxy)phenyl)phenyl acetate gave 4-(2-(α-D-mannopyranosyloxy)phenyl)phenyl acetic acid as a hygroscopic white solid.

$^1$H NMR: (300 MHz, DMSO-d6) 7.02–7.50 (comp, 8H), 5.30 (s, 1H), 3.30–3.75 (comp, 12H) ppm.

IR (KBr): 3404, 1788, 1712, 1486, 1218, 1170, 1018, 752 cm$^{-1}$.

m. p.: 65°–68° C.

Analysis: Calc for $C_{20}H_{22}O_8 \cdot [C_2HF_3O_2]$: 52.38% C, 4.59% H.

Found: 52.02% C, 4.52% H.

EXAMPLE 3

3-(2-(α-D-Mannopyranosyloxy)phenyl)benzoic acid, lithium salt

Part A:

Operating as in Part A in EXAMPLE 1, but employing 3-bromobenzoic acid gave methyl 3-bromobenzoate in 95% yield.

Part B:

Operating as in Part B in EXAMPLE 1, but employing methyl 3-bromobenzoate gave methyl 3-(2-methoxyphenyl)benzoate in 64% yield, m.p.: 92°–93° C.

Part C:

Operating as in Part C in EXAMPLE 1, but employing methyl 3-(2-methoxyphenyl)benzoate gave methyl 3-(2-hydroxyphenyl)benzoate in 84% yield.

Part D:

Operating as in Part D in EXAMPLE 1, but employing methyl 3-(2-hydroxyphenyl)benzoate gave methyl 3-(2-(2,3,4,6-tetra-O-acetyl-α-D-mannopyranosyloxy)-phenyl)benzoate in 85% yield.

Part E:

In a dry 50 ml flask under nitrogen, methyl 3-(2-(2,3,4,6-tetra-O-acetyl-α-D-mannopyranosyloxy)-phenyl)benzoate (2.18 g, 3.9 mmol) was dissolved in methanol (20 ml) and treated in one portion with sodium methoxide (250 mg) and the mixture was stirred at room temperature overnight, then concentrated under reduced pressure. The residue was purified by flash chromatography (SiO2, 7:3 methylene chloride/methanol) which gave methyl 3-(2-(α-D-mannopyranosyloxy)phenyl)benzoate in 84% yield.

Part F:

Methyl 3-(2-mannopyranosyloxy)phenyl)benzoate (0.662 g, 1.7 mmol) was dissolved in acetonitrile (15 ml). An aqueous solution of lithium hydroxide monohydrate (0.12 g, 2.55 mmol in 1 ml water) was added and the mixture was stirred at room temperature for 8 hours. The mixture was then diluted with additional acetonitrile (approximately 10 ml) and the lithium salt of 3-(2-(α-D-mannopyranosyloxyphenyl) benzoic acid precipitated. The solids were collected and dried which gave 0.614 g (94%) of product, m. p. 109°–115° C.

$^1$H NMR: (300 MHz, DMSO-d6) 8.11 (s, 1H), 7.79 (d, J=7 Hz, 1H), 7.20–7.40 (comp, 5H), 7.06 (t, J=7 Hz, 1H), 5.43 (s, 1H), 5.25 (br s, 1H), 5.04 (br s, 1H), 4.70 (br s, 1H), 4.55 (br s, 1H), 3.25–3.70 (comp, 6H) ppm. IR (KBr): 3384, 1560, 1405, 1389, 1111, 1057, 1020, 757 cm$^{-1}$.

Analysis: Calc for $C_{19}H_{19}O_8Li \cdot [H_2O] \cdot 1.8[LiOH]$: 51.4% C, 5.18% H.

Found: 51.62% C, 4.81% H.

EXAMPLE 4

4-(2-(α-D-Mannopyranosyloxy)phenyl)benzoic acid

Part A:

Operating as in Part A in EXAMPLE 1, but employing 4-bromobenzoic acid gave methyl 4-bromobenzoate in 90% yield, m.p. 66°–68° C.

Part B:

Operating as in Part B in EXAMPLE 1, but employing methyl 4-bromobenzoate gave methyl 4-(2-methoxyphenyl)benzoate in 51% yield.

Part C:

Operating as in Part C in EXAMPLE 1, but employing methyl 4-(2-methoxyphenyl)benzoate gave methyl 4-(2-hydroxyphenyl)benzoate in 71% yield.

Part D:

Operating as in Part D in EXAMPLE 1, but employing methyl 4-(2-hydroxyphenyl)benzoate gave methyl 4-(2-(2,3,4,6-tetra-O-acetyl-α-D-mannopyranosyloxy-phenyl)benzoate in 95% yield.

Part E:

Operating as in Part E in EXAMPLE 1, but employing methyl 4-(2-(2,3,4,6-tetra-O-acetyl-α-D-mannopyranosyloxy) phenyl)benzoate gave 4-(2-(α-D-mannopyranosyloxy)phenyl)benzoic acid in 71% yield, m.p. 248°–249° C.

$^1$H NMR: (300 MHz, DMSO-d6) 7.98 (d, J=8 Hz, 2H), 7.61 (d, J=8 Hz, 2H), 7.30–7.40 (comp, 3H), 7.05–7.16 (comp, 1H), 5.36 (s, 1H), 4.90–5.05 (br s, 1H), 4.76–4.90 (br s, 1H), 4.65–4.76 (br s, 1H), 4.40–4.58 (br s, 1H), 3.25–3.70 (comp, 6H) ppm.

IR (KBr): 3511, 3398, 2929, 1683, 1614, 1485, 1419, 1314, 1259, 1107, 1013, 986, 746 cm$^{-1}$.

Analysis: Calc for $C_{19}H_{20}O_8 \cdot 0.25 [H_2O]$: 59.92% C, 5.43% H.

Found: 59.80% C, 5.25% H.

EXAMPLE 5

3-(2-(α-D-Mannopyranosyloxy)phenyl)phenyloxyacetic acid

Part A:

3-Bromophenol (2.84 g, 16.4 mmol) was dissolved in dimethylformamide (50 ml) in a dry 100 ml flask under nitrogen. Sodium hydride (0.7 g of a 60% suspension in mineral oil, washed with hexane, 16.7 mmol) was added in portions and the mixture was stirred for one hour at room temperature. Ethyl bromoacetate (1.85 ml, 16.7 mmol) was added drop-wise and the reaction was stirred overnight at room temperature. Approximately two-thirds of the solvent was removed under reduced pressure and the residue was mixed with water (150 ml) and extracted with methylene chloride (3×20 ml). The extracts were combined, washed with water (50 ml), saturated sodium chloride solution (50 ml), then dried (MgSO$_4$). The solution was filtered and concentrated which gave 4.18 g (98%) of ethyl 3-bromophenyloxyacetate.

Part B:

Operating as in Part B in EXAMPLE 2, but employing ethyl 3-bromophenyloxyacetate gave ethyl 3-(2-hydroxyphenyl)phenyloxyacetate in 52% yield.

Part C:

Operating as in Part D in EXAMPLE 1, but employing ethyl 3-(2-hydroxyphenyl)phenyloxyacetate gave ethyl 3-(2-(2,3,4,6-tetra-O-acetyl-α-D-mannopyranosyloxy)phenyl)phenyloxyacetate in 69% yield.

Part D:

Operating as in Part E in EXAMPLE 1, but employing ethyl 3-(2-(2,3,4,6-tetra-O-acetyl-α-D-mannopyranosyloxy)phenyl)phenyloxyacetate gave 3-(2-(α-D-mannopyranosyloxy)phenyl)phenyloxyacetic acid in 82% yield, m.p. 58°–60° C.

$^1$NMR: (300 MHz, DMSO-d6) 7.25–7.38 (comp, 4H), 7.06–7.15 (comp, 2H), 6.97 (s, 1H), 6.90 (mult, 1H), 5.34 (mult, 1H), 4.70 (s, 2H), 3.80–4.40 (br s, 4H), 3.30–3.75 (comp, 6H) ppm.

IR (KBr): 3404, 2943, 1788, 1737, 1478, 1424, 1220, 1173, 1068, 1016, 979, 755, 696 cm$^{-1}$.

Analysis: Calc for $C_{20}H_{22}O_9 \cdot [H_2O]1.1 [C_2HF_3O_2]$: 48.50% C, 4.60% H.

Found: 48.70% C, 4.21% H.

EXAMPLE 6

4-(2-(α-D-Mannopyranosyloxy)phenyl)phenyloxyacetic acid

Part A:

Operating as in Part A in EXAMPLE 5, but employing 4-bromophenol gave ethyl 4-bromophenyloxyacetate in 98% yield.

Part B:

Operating as in Part B in EXAMPLE 2, but employing ethyl 4-bromophenyloxyacetate gave ethyl 4-(2-hydroxyphenyl)phenyloxyacetate in 41% yield.

Part C:

Operating as in Part D in EXAMPLE 1, but employing ethyl 4-(2-hydroxyphenyl)phenyloxyacetate gave ethyl 4-(2-(2,3,4,6-tetra-O-acetyl-α-D-mannopyranosyloxy)phenyl)phenyloxyacetate in 80% yield.

Part D:

Operating as in Part E in EXAMPLE 1, but employing ethyl 4-(2-(2,3,4,6-tetra-O-acetyl-α-D-mannopyranosyloxy)phenyl)phenyloxyacetate gave 4-(2-(α-D-mannopyranosyloxy)phenyl)phenyloxyacetic acid in 69% yield, m.p.: 145°–146° C.

$^1$H NMR: (300 MHz, DMSO-d6) 7.42 (d, J=8Hz, 2H), 7.23–7.35 (comp, 3H), 7.07 (t, J=7 Hz, 1H), 6.95 (d, J=8 Hz, 2H), 5.30 (s, 1H), 4.71 (s, 2H), 3.30–3.80 (comp, 10H) ppm.

IR (KBr): 3418, 2930, 1739, 1521, 1486, 1240, 1219, 1110, 1068, 1013, 834, 756 cm$^{-1}$.

Analysis: Calc for $C_{20}H_{22}O_9 \cdot 1.5[H_2O]$: 55.43% C, 5.81% H.

Found: 55.81% C, 5.54% H.

EXAMPLE 7

3-(2-(α-D-Mannopyranosyloxy)phenyl)benzyloxyacetic acid

Part A:

Operating as in Part A in EXAMPLE 5, but employing 3-bromobenzylalcohol gave ethyl 3-bromobenzyloxyacetate in 40% yield.

Part B:

Operating as in Part B in EXAMPLE 2, but employing ethyl 3-bromobenzyloxyacetate gave ethyl 3-(2-hydroxyphenyl)benzyloxyacetate in 34% yield.

Part C:

Operating as in Part D in EXAMPLE 1, but employing ethyl 3-(2-hydroxyphenyl)benzyloxyacetate gave ethyl 3-(2-(2,3,4,6-tetra-O-acetyl-α-D-mannopyranosyloxy)phenyl)benzyloxyacetate in 74% yield.

Part D:

Operating as in Part E in EXAMPLE 1, but employing ethyl 3-(2-(2,3,4,6-tetra-O-acetyl-α-D-mannopyranosyloxy)phenyl)benzyloxyacetate gave 3-(2-(α-D-mannopyranosyloxy)phenyl)benzyloxyacetic acid in 30% yield, m.p. 77°–78° C.

$^1$HNMR: (300 MHz, DMSO-d6) 7.20–7.51 (comp, 7H), 7.15 (mult, 1H), 5.32 (s, 1H), 4.11 (s, 2H), 3.25–3.75 (comp, 6H), 3.47 (s, 2H) ppm.

IR (KBr): 3417, 2938, 1787, 1734, 1220, 1172, 1112, 1013, 977, 754 cm$^{-1}$.

MS(FAB): 443.2 (m+Na)$^+$

Analysis: Calc for $C_{21}H_{29}O_9 \cdot [C_2HF_3O_2]$, 0.5[H$_2$O]: 50.83% C, 4.82% H.

Found: 50.59% C, 4.74% H.

EXAMPLE 8

N-(4-(2T(α-D-Mannopyranosyloxy)phenyl)benzoyl)glycine

Part A:

Acetone (5.6 ml) and dimethoxypropane (5.6 ml) were added to 4-(2-(α-D-mannopyranosyloxy) phenyl)-benzoic acid (0.54 g, 1.43 mmol) to form a heterogeneous mixture. A catalytic amount of p-toluenesulfonic acid monohydrate was introduced and the reaction was stirred at room temperature for 45 minutes, at which point a clear, homogeneous solution was obtained. The solvent was removed in vacuo and the yellow oily residue taken up in ethyl acetate, washed with saturated sodium bicarbonate then saturated sodium chloride, dried (MgSO$_4$) and concentrated in vacuo to afford 4-(2-(2,3:4,6-di-O-isopropylidene)α-D-mannopyranosyloxy)phenyl)benzoic acid (0.70 g).

Part B:

A solution of crude 4-(2-(2,3:4,6-di-O-isopropylidene)α-D-mannopyranosyloxy)phenyl)benzoic acid (0.70 g) in dry dichloromethane (4 ml) was added to a slurry of glycine ethyl ester hydrochloride (0.20 g, 1.44 mmol) and triethylamine (0.40 ml, 2.88 mmol) in dry dichloromethane (3 ml). N-Hydroxysuccinimide 0.16 g, 1.44 mmol) and N,N'-dicyclohexylcarbodiimide (0.32 g, 1.55 mmol) were added and the reaction mixture stirred under nitrogen at room temperature for 4 hours. Precipitated dicyclohexylurea was filtered away and the filtrate diluted with dichloromethane. The resulting solution was washed successively with water, 1N HCl, saturated sodium bicarbonate and brine, then dried (MgSO$_4$) and concentrated under reduced pressure to afford 0.69g (89% for two steps) of N-(4-(2-(2,3:4,6-di-O-isopropylidene)α-D-mannopyranosyloxy)phenyl)benzoyl) glycine ethyl ester.

Part C:

N-(4-(2-(2,3:4,6-di-O-isopropylidene)α-D-mannopyranosyloxy)phenyl)benzoyl) glycine ethyl ester (0.69 g, 1.28 mmol) was dissolved in tetrahydrofuran (2.5 ml). An equal volume of 1N HCl was added and the reaction mixture stirred overnight. 2N sodium hydroxide (2 ml) was added and the reaction stirred for another 8 hours. The solution was then reacidified to pH 4.5 with 1N HCl and the product isolated by preparative reverse-phase HPLC on a Dynamax 300 Å 5 micron (21 mm ID×25 cm) C$_{18}$ column. A gradient of 5–50% solvent B was run over 20 minutes at a flow rate of 10 ml/min, where solvent A was composed of 5% acetonitrile/water with 0.1% TFA and solvent B was composed of 95% acetonitrile/water with 0.1% TFA. The effluent was monitored at 254 nm. Pure fractions were combined and lyophilized to yield 0.33 g of N-(4-(2-(α-D-mannopyranosyloxy)phenyl)benzoyl) glycine.

$^1$HNMR: (300 MHz, D$_2$O) 7.85 (d, J=7.8, 2H), 7.61 (d, J=7.8, 2H), 7.41 (m, 2H), 7.32 (d, J=9.0, 1H), 7.20 (t, J=6.9, 7.8, 1H), 5.48 (s, 1H), 4.11 (s, 2H) 3.94 (s, 1H), 3.60 (br m, 4H), 3.28 (br m, 1H).

IR (KBr): 3404, 2938, 1734, 1637, 1544, 1220, 1107, 1066 cm$^{-1}$ m.p.: 127°–129° C.

Analysis: Calc for C$_{21}$H$_{23}$NO$_9$. 1/5[CF$_3$CO$_2$H]; 56.34% C, 5.13% H, 3.07% N.

Found: 56.36% C, 4.93% H, 2.98% N.

EXAMPLE 9

N-(4-(2-(α-D-Mannopyranosyloxy)phenyl)benzoyl)-D-phenylalanine

Part A:

4-(2-(2,3:4,6-Di-O-isopropylidene-α-D-mannopyranosyloxy)phenyl)benzoic acid (0.25g, 0.55 mmol) and D-phenylalanine methyl ester hydrochloride (0.13 g, 0.60 mmol) were slurried under dry dichloromethane (2 ml). N-methylmorpholine (0.13 ml, 1.18 mmol), hydroxybenzotriazole hydrate (74 mg, 0.55 mmol) and 1-(3-dimethylaminopropyl)-3-ethylcarbodiimide hydrochloride (0.26 g, 1.35 mmol) were added and the reaction was stirred at room temperature for two hours. Ethyl acetate was added and the solution was washed with water, 1N HCl, saturated sodium bicarbonate solution, brine, dried (MgSO$_4$) and concentrated in vacuo. The residue was purified by silica gel chromatography (2:1 hexane:ethyl acetate) to afford N-(4-(2-(2,3:4,6-di-O-isopropylidene-α-D-mannopyranosyloxy)phenyl)benzoyl)-D-phenylalanine methyl ester (0.26 g, 76%) as a white foam.

Part B:

Operating in a manner analogous to Part C of EXAMPLE 8, but employing an HPLC gradient of 20–80% solvent B in 20 minutes gave N-(4-(2-(α-D-mannopyranosyloxy)phenyl)benzoyl)-D-phenylalanine in 46% yield; m.p.=116°–119° C.; IR (KBr): 3424, 2972, 1738, 1642, 1539, 1361, 1215, 1109, 1070, 1013 cm$^{-1}$; $^1$H NMR (300 MHz, CD$_3$OD): δ7.77 (d, 2H, J=8.4), 7.54 (d, 2H, J=8.4), 7.29 (m, 9H), 7.10 (t, 1H), 5.41 (s, 1H), 3.80 (br s, 1H), 3.67 (m, 4H), 3.49 (br m, 1H), 3.35 (m, 1H), 3.12 ppm (dd, 2H, J=13.8, 9.6); MS (CI): m/z=524, 362, 163; analysis: calc. for C$_{28}$H$_{29}$NO$_9$, 64.2% C, 5.6% H, 2.7% N; found: 64.2% C, 5.6% H, 2.4% N.

EXAMPLE 10

3-(2-(6-Azido-6-deoxy-α-D-mannopyranosyloxy)phenyl) phenylacetic acid

Part A:

Methyl 3-(2-(2,3,4,6-tetra-O-acetyl-α-D-mannopyranosyloxy)phenyl)phenylacetate (3.96 g, 6.9 mmol, from Part E, EXAMPLE 2) was dissolved in methanol (50 ml), sodium methoxide (100 mg) was added and the solution stirred at room temperature for two hours. The reaction mixture was neutralized with Dowex-50W ion exchange resin (H+ form), filtered and concentrated in vacuo. Chromatography (silica, 9:1 CHCl$_3$:methanol) gave methyl 3-(2-(α-D-mannopyranosyloxy)phenyl)phenylacetate (2.8 g, quantitative yield (~100%)).

Part B:

Methyl 3-(2-(α-D-mannopyranosyloxy) phenyl)phenylacetate (1.86 g, 4.6 mmol) was dissolved in 2,2-dimethoxypropane (30 ml) and acetone (30 ml). p-Toluenesulfonic acid (100 mg) was added and the solution stirred at room temperature overnight. The reaction mixture was poured into saturated sodium bicarbonate and the product extracted with ethyl acetate. The combined extracts were dried (MgSO$_4$) and concentrated in vacuo. Purification by chromatography (silica, eluent 6:1 hexane:ethyl acetate) gave methyl 3-(2-(2,3:4,6-di-O-isopropylidene-α-D-mannopyranosyloxy)phenyl)phenylacetate (1.87 g, 84%).

Part C:

Methyl 3-(2-(2,3:4,6-di-O-isopropylidene-α-D-mannopyranosyloxy)phenyl)phenylacetate (1.53 g, 3.2 mmol) was dissolved in methanol (50 ml), p-toluenesulfonic acid (100 mg) added and stirred at room temperature until t.l.c. (eluent 9:1 CHCl$_3$:methanol) showed optimum conversion to the monoacetonide. The reaction was quenched by the addition of a small volume of saturated sodium bicarbonate and then concentrated under reduced pressure. The residue was partitioned between ethyl acetate and water and the aqueous layer extracted with ethyl acetate. The combined organic layers were washed once with saturated sodium chloride, dried over magnesium sulfate and concentrated under reduced pressure. Chromatography (silica, eluent 9:1 CHCl$_3$:methanol) gave methyl 3-(2-(2,3-O-isopropylidene-α-D-mannopyranosyloxy)phenyl)phenylacetate (0.92 g, 55%).

Part D:

Methyl 3-(2-(2,3-O-isopropylidene-α-D-mannopyranosyloxy)phenyl)phenylacetate (6.37 g, 14.3 mmol) was dissolved in pyridine (100 ml) and the solution cooled to 0° C. p-Toluenesulfonyl chloride (5.5 g, 28.9 mmol) was added followed by 4dimethylaminopyridine (100 mg) and the solution stirred at room temperature overnight. After cooling to 0° C., acetic anhydride (5 ml, 53 mmol) was added and the solution stirred at room temperature for 24 hours. The reaction mixture was diluted with ethyl acetate and washed with dilute hydrochloric acid to remove the pyridine. The organic layer was then washed with dilute sodium bicarbonate and saturated sodium chloride, dried (MgSO$_4$) and concentrated in vacuo. This gave methyl 3-(2-(4-O-acetyl-2,3-O-isopropylidene-6-O-α-toluenesulfonyl-α-D-mannopyranosyloxy)phenyl)phenylacetate (9.19 g, quantitative yield (~100%)).

Part E:

Methyl 3-(2-(4-O-acetyl-2,3-O-isopropylidene-6-O-p-toluenesulfonyl-α-D-mannopyranosyloxy)phenyl)phenylacetate (9.19 g, 14.4 mmol) was dissolved in dimethylformamide (100 ml), sodium iodide (4.3 g, 29 mmol) was added and the mixture heated at 110° C. for 6 hours. After cooling to room temperature most of the DMF was removed in vacuo and the residue partitioned between ethyl acetate and water. The organic layer was washed with water, dilute sodium thiosulfate solution, water, saturated sodium chloride, dried (MgSO$_4$) and concentrated in vacuo. Chromatography (silica, eluent 2:1 hexane:ethyl acetate) gave methyl 3-(2-(4-O-acetyl-6-iodo-6-deoxy-2,3-O-isopropylidene-α-D-mannopyranosyloxy)phenyl)phenylacetate (6.42 g, 75%).

Part F:

Methyl 3-(2-(4-O-acetyl-6-azido-6-deoxy-2,3-O-isopropylidene-α-D-mannopyranosyloxy)phenyl) phenylacetate was prepared from methyl 3-(2-(4-O-acetyl-6-iodo-6-deoxy-2,3-O-isopropylidene-α-D-mannopyranosyloxy)phenyl)phenylacetate and sodium azide in 93% yield using an analogous procedure to Part E, of this Example, with sodium azide being used in place of sodium iodide.

Part G:

Methyl 3-(2-(4-O-acetyl-6-azido-6-deoxy-2,3-O-isopropylidene-α-D-mannopyranosyloxy)phenyl) phenylacetate (0.208 g, 0.41 mmol) was dissolved in methanol (6 ml) and water (2 ml). Concentrated hydrochloric acid (3 drops) was added and the solution stirred at room temperature for two days. The solution was made basic with dilute sodium hydroxide solution and stirred at room temperature for one hour. After neutralizing with dilute hydrochloric acid the solution was concentrated in vacuo. The residue was shaken with methanol and the white solid removed by centrifugation. The solution was concentrated under reduced pressure and the residue taken up in 5% acetonitrile/water with 0.1% in trifluoroacetic acid. After adjusting the pH to 3.5 using dilute hydrochloric acid the product was purified by preparative reverse-phase HPLC on a Dynamax 300 Å 5 micron C18 column (21.4×250 mm) at a flow rate of 10 ml/min. An elution gradient of 20–80% solvent B over 30 minutes was used, with solvent B composed of 95% acetonitrile/water with 0.1% trifluoroacetic acid and solvent A composed of 5% acetonitrile/water with 0.1% trifluoroacetic acid. The effluent was monitored at 254 nm, and pure fractions were combined and lyophilized to yield methyl 3-(2-(6-azido-6-deoxy-α-D-mannopyranosyloxy)phenyl)phenylacetic acid, (44 mg, 26%); $^1$HNMR (300 MHz, D$_2$O/DMSO-d$_6$) δ3.3–3.4 (m, 3H, OH), 3.55 (dd, J=9.6, 8.4, 1 H, CH$_2$N$_3$), 3.62 (dd, J=9.6, 2.7, 1 H, CH$_2$N$_3$), 3.73 (s, 2H, CH$_2$CO$_2$H), 3.96 (m, 1H), 4.6–5.0 (m , 3H), 5.46 (s, 1H), 7.14–7.50 (m, 8H, arom.). IR (KBr: cm$^{m-1}$): 3421, 2101, 1717; Mass Spectrum m/e (CI: CH$_4$) 229, 183 (100%). Anal. Calcd. for C$_{20}$H$_{21}$N$_3$O$_7$.0.3 [CF$_3$CO$_2$H]: C, 55.9; H, 4.9N, 9.6; Found: C, 56.1; H, 4.6; N, 9.5%.

EXAMPLE 11

3-(2-(6-Amino-6-deoxy-α-D-mannopyranosyloxy)-phenyl)phenylacetic acid, hydrochloride Part A:

Methyl 3-(2-(4-O-acetyl-6-azido-6-deoxy-2,3-O-isopropylidene-α-D-mannopyranosyloxy)phenyl)phenylacetate (1.26 g, 2.5 mmol, from part F, EXAMPLE 10) was stirred with sodium methoxide (100 mg) in methanol (15 ml) at room temperature overnight. The solution was neutralized with Dowex-50W ion exchange resin (H$^+$ form), filtered and concentrated in vacuo. Chromatography (silica, eluent 3:1 hexane:ethyl acetate) gave methyl 3-(2-(6-azido-6-deoxy-2,3-O-isopropylidene-α-D-mannopyranosyloxy)phenyl)phenylacetate (1.02 g, 88%).

Part B:

Methyl 3-(2-(6-azido-6-deoxy-2,3-O-isopropylidene-α-D-mannopyranosyloxy)phenyl)phenylacetate (0.79 g, 1.7 mmol) was dissolved in methanol (20 ml), Raney nickel (0.56 g) was added and the mixture stirred at room temperature for two hours. The mixture was filtered and concentrated in vacuo. Chromatography (silica, eluent 9:1 CHCl$_3$/methanol) gave methyl 3-(2-(6-amino-6-deoxy-2,3-O-isopropylidene-α-D-mannopyranosyloxy)phenyl)phenylacetate 0.52 g (69%).

Part C:

Methyl 3-(2-(6-amino-6-deoxy-2,3-O-isopropylidene-α-D-mannopyranosyloxy)phenyl)phenylacetate (77 mg, 0.17 mmol) was dissolved in methanol (5 ml), p-toluenesulfonic acid (40 mg, 0.21 mmol) was added and the solution stirred at room temperature overnight. Aqueous sodium hydroxide (2M, 0.4 ml) was added and the solution stirred for 5 minutes before acidifying with dilute hydrochloric acid. The product was purified by preparative reverse-phase HPLC on a Dynamax 300 Å 5 micron C18 column (21.4×250 mm) at a flow rate of 10 ml/min. An elution gradient of 10–40% solvent B over 25 minutes was used, with solvent B composed of 95% acetonitrile/water with 0.1% trifluoroacetic acid and solvent A composed of 5% acetonitrile/water with 0.1% trifluoroacetic acid. The effluent was monitored at 254 nm, and pure fractions were combined and concentrated in vacuo. Water (5 ml) and dilute hydrochloric acid (0.2 ml) were added and the mixture re-concentrated. This procedure was repeated once more with hydrochloric acid and once with water. The residue was then dissolved in water (5 ml) and lyophilized to yield 3-(2-(6-amino-6-deoxy-α-D-mannopyranosyloxy)-phenyl)phenylacetic acid, hydrochloride (50.3 mg, 74%).

EXAMPLE 12

N-(3-(2-(α-D-Mannopyranosyloxy)phenyl)benzoyl)-L-glutamic acid

Part A:

3-(2-(2,3:4,6-Di-O-isopropylidene-α-D-mannopyranosyloxy)phenyl)benzoic acid can be prepared in a manner analogous to Part A of EXAMPLE 8.

Part B:

Operating in a manner analogous to Part A of EXAMPLE 9, but employing L-glutamic acid dimethyl ester hydrochloride and 3-(2-(2,3:4,6-di-O-isopropylidene-α-D-mannopyranosyloxy)phenyl)benzoic acid gave N-(3-(2-(2,3:4,6-di-O-isopropylidene-α-D-mannopyranosyloxy) phenyl)benzoyl)-L-glutamic acid dimethyl ester in 89% yield.

Part C:

Operating in a manner analogous to Part C of EXAMPLE 8, but employing an HPLC gradient of 10–60% solvent B in 20 minutes gave N-(3-(2-(α-D-mannopyranosyloxy)phenyl)benzoyl)-L-glutamic acid in 19% yield; m.p.=109°–112° C.; IR (KBr): 3390, 2938, 1717, 1635, 1539, 1416, 1217, 1100, 1059, 1011 cm$^{-1}$; $^1$H NMR (300 MHz, D$_2$O): δ 7.82 (s, 1H), 7.73 (d, 1H, J=7.8), 7.65 (d, 1H, J=7.5), 7.53 (t, 1H, J=7.5), 7.37 (d, 2H, J=7.8), 7.29 (d, 1H, J=8.1), 7.17 (t, 1H, J=7.2), 5.45 (s, 1H), 4.58 (q, 1H, J=4.8), 3.92 (s, 1H), 3.57 (m, 6H), 3.19 (br m, 1H), 2.52 (t, 2H, J=7.2), 2.27 (m, 1H), 2.11 ppm (m, 1H); Mass Spectrum m/e (CI:CH$_4$) 344, 163; analysis: calc. for C$_{24}$H$_{27}$NO$_{11}$.1/3 [C$_2$F$_3$HO$_2$], 54.5% C, 5.1% H, 2.6% N; found: 54.4% C, 4.8% H, 2.6% N.

EXAMPLE 13

3-(2-(6-(Carboxymethylthio)-6-deoxy-α-D-mannopyranosyloxy)phenyl)phenylacetic acid Part A:

Sodium hydride (60% wt. disp., 0.14 g, 3.4 mmol) was washed with hexane, tetrahydrofuran (5 ml) was added and the mixture degassed. Methyl thioglycolate (0.4 ml, 4.5 mmol) was added, followed by a solution of methyl 3-(2-(4-O-acetyl-6-deoxy-6-iodo-2,3-O-isopropylidene-α-D-mannopyranosyloxy)phenyl) phenylacetate (0.83 g, 1.4 mmol, Part E, EXAMPLE 10) in THF (10 ml). The solution was degassed again and then stirred at room temperature for 72 hours. The reaction was quenched with water then partitioned between ethyl acetate and water. The organic layer was washed with dilute sodium thiosulphate, water and saturated sodium chloride. After drying (MgSO$_4$), the solution was concentrated in vacuo. Chromatography (silica, eluent 2:1 hexane:ethyl acetate) gave methyl 3-(2-(4-O-acetyl-6-(carbomethoxymethylthio)-6-deoxy-2,3-O-isopropylidene)-α-D-mannopyranosyloxy)phenyl)phenylacetate (0.7 g, 87%).

Part B:

Methyl 3-(2-(4-O-acetyl-6-(carbomethoxymethylthio)-6-deoxy-2,3-O-isopropylidene-α-D-mannopyranosyloxy)phenyl)phenylacetate (0.56 g, 1 mmol) was dissolved in methanol (30 ml), dilute hydrochloric acid (2 ml) was added and stirred at room temperature overnight, then warmed to reflux for 30 minutes. After cooling to room temperature, sodium hydroxide (2M, 5 ml) was added and the solution stirred for 10 minutes. The solution was neutilized using dilute hydrochloric acid and then concentrated in vacuo. The residue was shaken with methanol and the white solid removed by centrifugation. The solution was concentrated in vacuo and the residue taken up in 5% acetonitrile/water with 0.1% trifluoroacetic acid. After adjusting the pH to 3.5 using dilute hydrochloric acid the product was purified by preparative reverse-phase HPLC on a Dynamax 300 Å 5 micron C18 column (21.4×250 mm) at a flow rate of 10 ml/min. An elution gradient of 20–80% solvent B over 20 minutes was used, with solvent B composed of 95% acetonitrile/water with 0.1% trifluoroacetic acid and solvent A composed of 5% acetonitrile/water with 0.1% trifluoroacetic acid. The effluent was monitored at 254 nm, and pure fractions were combined and lyophilized to yield 3-(2-(6(carboxymethylthio)-6-deoxy-α-D-mannopyranosyloxy)phenyl)phenylacetic acid (0.40 g, 83%); $^1$H NMR (300 MHz, D$_2$O): δ2.60 (dd, J=14.1, 8.4, 1 H, 6-H), 2.84 (dd, J=14.1, 1.8, 1H, 6'-H), 3.04 and 3.30 (both d, J=14.4, 1H, SCH$_2$CO$_2$H), 3.3–3.6 (m, 3H), 3.70 (s, 2H, CH$_2$CO$_2$H), 3.94 (m, 1H), 4.6–5.0 (m , 3H), 5.48 (s, 1 H, 1-H), 7.14–7.50 (m, 8H, arom.); IR (KBr: cm$^{-1}$): 3396, 1710; Mass spectrum m/e (CI: CH$_4$) 465 (1%), 393, 229, 183 (100%). Anal. calcd for C$_{22}$H$_{24}$O$_9$S. 0.8 [H$_2$O]: C, 55.2; H, 5.4. Found: C, 55.25; H, 5.25%.

EXAMPLE 14

2-(3-(2-(α-D-Mannopyranosyloxy)phenyl)phenyl)ethanesulfonic acid

Part A:

Methyl 3-(2-(2,3:4,6-di-O-isopropylidene-α-D-mannopyranosyloxy)phenyl)phenylacetate (1.28 g, 2.6 mmol, from Part B, EXAMPLE 10) was dissolved in ether (50 ml) and cooled to 0° C. Lithium aluminum hydride (1M in THF, 50 ml, 5 mmol) was added dropwise and the solution stirred for 10 minutes. The reaction was quenched by careful addition of water, followed by ice cold dilute sulfuric acid. The organic layer was washed with water, then saturated sodium bicarbonate solution, dried (MgSO$_4$) and concentrated in vacuo. to give 2-(3-(2-(2,3:4,6-di-O-isopropylidene-α-D-mannopyranosyloxy)phenyl)phenyl)ethanol (1.13 g, 94%).

Part B:

2-(3-(2-(2,3:4,6-Di-O-isopropylidene-α-D-mannopyranosyloxy)phenyl)phenyl)ethanol (0.73 g, 1.6 mmol) was dissolved in dichloromethane (50 ml) and cooled to 0° C. Triethylamine (0.33 ml, 2.4 mmol) was added, followed by methanesulfonyl chloride (0.15 ml, 1.9 mmol). After five minutes at 0° C. the reaction mixture was diluted with dichloromethane and washed with dilute hydrochloric acid, water and saturated sodium bicarbonate solution, dried (MgSO$_4$) and concentrated in vacuo to give 2-(3-(2-(2,3:4,6-di-O-isopropylidene-α-D-mannopyranosyloxy)phenyl)phenyl)ethanol 1-O-methanesulfate (0.77 g, 90%).

Part C:

2-(3-(2-(2,3:4,6-Di-O-isopropylidene-α-D-mannopyranosyloxy)phenyl)phenyl)ethanol 1-O-methanesulfonate (0.22 g, 0.4 mmol) was dissolved in ethanol (5 ml), potassium thioacetate (0.1 g, 0.88 mmol) added and the mixture heated at 80° C. for 30 minutes. After cooling to room temperature the reaction mixture was partitioned between ethyl acetate and water. The organic layer was washed twice with water, dried (MgSO$_4$) and concentrated in vacuo. Chromatography (silica, eluent 2:1 hexane: ethyl acetate) gave 2-mercapto-(3-(2-(2,3: 4,6-di-O-isopropylidene-α-D-mannopyranosyloxy)-phenyl)phenyl)ethane S-acetate (0.17 g, 80%).
Part D:

2-Mercapto-(3-(2-(2,3: 4,6-di-O-isopropylidene-α-D-mannopyranosyloxy)phenyl)phenyl)ethane S-acetate (0.15 g, 0.29 mmol) was dissolved in methanol (1 ml). A solution of Oxone (approx. 1 meq/ml in methanol/water, 1.5 ml) was added dropwise at room temperature over the course of 90 minutes. After stirring for 7 days another portion of Oxone solution (1 ml) was added over the course of 60 minutes and stirring was continued for another 3 days. The product was isolated by preparative reverse-phase HPLC on a Dynamax 300 Å 5 micron C18 column (21×250 mm). A gradient of 0–70% solvent B was run over 20 minutes at a flow rate of 10 ml/min, where solvent B was composed of 95% acetonitrile/water with 0.1% trifluoroacetic acid and solvent A was composed of 5% acetonitrile/water with 0.1% trifluoroacetic acid. The effluent was monitored at 254 nm, and pure fractions were combined and lyophilized to give 2-(3-(2-α-D-mannopyranosyloxyphenyl)-phenyl)ethanesulfonic acid (50.8 mg, 38%); $^1$H NMR (300 MHz, $D_2O$): δ7.36 (m, 8H), 7.17 (t, 1H, J=7.5), 5.44 (s, 1H), 3.93 (s, 1H), 3.61 (m, 1H), 3.57 (m, 4H), 3.25 (br m, 1H), 3.10 ppm (m, 4H); Mass Spectrum m/e (CI:$CH_4$) 279, 163; anal. calcd for $C_{20}H_{24}SO_9 \cdot 2[H_2O]$, 50.4% C, 5.9% H; found: 50.4% C, 6.0% H.

EXAMPLE 15

N-(4-(2-(α-D-Mannopyranosyloxy)phenyl)benzoyl)-L-glutamic acid
Part A:

Operating in a manner analogous to Part A of EXAMPLE 9, but employing L-glutamic acid dimethyl ester hydrochloride gave N-(4-(2-(2,3:4,6-di-O-isopropylidene)-α-D-mannopyranosyloxyphenyl)benzoyl)-L-glutamic acid dimethyl ester in 89% yield.
Part B:

Operating in a manner analogous to Part C of EXAMPLE 8, but employing an HPLC gradient of 10–60% solvent B in 20 minutes gave N-(4-(2-(α-D-mannopyranosyloxy)phenyl)benzoyl)-L-glutamic acid in 43% yield; m.p.=118°–121° C.; IR (KBr): 3390, 2938, 1717, 1635, 1539, 1477, 1217, 1107, 1059, 1011 cm$^{-1}$; $^1$H NMR (300 MHz, $CD_3OD$): δ7.80 (d, 2H, J=8.7), 7.55 (d, 2H, J=8.4), 7.35 (m, 2H), 7.30 (d, 1H, J=8.1), 7.18 (t, 1H, J=7.5), 5.46 (s, 1H), 4.58 (dd, 1H, J=9.9, 5.7), 3.93 (s, 1H), 3.60 (m, 5H), 3.24 (br m, 1H), 2.53 (t, 2H, J=7.2), 2.27 (m, 1H), 2.12 ppm (m, 1H); Mass Spectrum m/e (CI:$CH_4$) 344, 163; analysis: calc. for $C_{24}H_{27}NO_{11} \cdot 6,34.1/4[C_2F_3HO_2]$, 54.0% C, 5.1% H, 2.6% N; found: 53.7% C, 5.1% H, 2.4% N.

EXAMPLE 16

N-(4-(2-(α-D-Mannopyranosyloxy)phenyl)benzoyl)-β-alanine
Part A:

Operating in a manner analogous to Part A of EXAMPLE 9, but employing β-alanine ethyl ester hydrochloride gave N-(4-(2-(2,3:4,6-di-O-isopropylidene)-α-D-mannopyranosyloxyphenyl)benzoyl)-β-alanine ethyl ester in 58% yield.
Part B:

Operating in a manner analogous to Part C of EXAMPLE 8, but employing an HPLC gradient of 0–50% solvent B in 20 minutes gave N-(4-(2-(α-D-mannopyranosyloxy)phenyl)benzoyl)-β-alanine in 53% yield; m.p.=101°–104° C.; IR (KBr): 3397, 2938, 1717, 1635, 1539, 1484, 1217, 1107, 1066, 1011 cm$^{-1}$;

$^1$H NMR (300 MHz, $D_2O$): δ7.75 (d, 2H, J=8.1), 7.54 (d, 2H, J=7.8), 7.35 (m, 3H), 7.19 (t, 1H, J=7.5), 5.47 (s, 1H), 3.93 (s, 1H), 3.64 (m, 7H), 3.26 (br m, 1H), 2.69 ppm (t, 2H, J=6.4); Mass Spectrum m/e (CI:$CH_4$) 448, 286, 163; analysis: calc. for $C_{22}H_{25}NO_9 \cdot 1/3[C_2F_3HO_2]$, 56.1% C, 5.3% H, 2.9% N; found: 56.1% C, 5.1% H, 3.0% N.

EXAMPLE 17

3-(3-(α-D-Mannopyranosyloxymethyl)phenyl)phenylacetic acid
Part A:

3-Bromobenzyl alcohol (2.0 g, 10.7 mmol) was dissolved in dry THF (50 ml) in a dry 100 ml flask flushed with nitrogen. The mixture was chilled in a dry ice/acetone bath. n-Butyl lithium (11 ml of a 2.13M solution in hexane, 23.5 mmol) was added. The reaction was warmed to room temperature for 1 hour, then cooled in an ice water bath. Trimethyl borate (1.3 ml, 11.2 mmol) was added and the mixture was stirred at room temperature overnight, then treated with 2N aqueous HCl to pH 2, and stirred for 3 hours. Brine (15 ml) was added, and the mixture was extracted with ethyl acetate (3×15 ml). The organic materials were combined, dried ($MgSO_4$) then concentrated under reduced pressure which gave of 3-hydroxymethylbenzeneboronic acid (98%) as a clear oil.

3-Hydroxymethylbenzeneboronic acid (1.8 g, 11.8 mmol), 3-bromophenylacetic acid (2.55 g, 11.8 mmol), tribasic potassium phosphate, (7.54 g, 35.5 mmol), DMF (55 ml), and water (20 ml) were degassed under nitrogen in a 250 ml flask fitted with a reflux condenser. Bis[triphenylphosphine]palladium(II) chloride (0.17 g, 0.24 mmol) was added. The mixture was degassed under nitrogen, and heated at 90° C. overnight, then acidified with 2N HCl, mixed with brine (15 ml), and extracted with methylene chloride (3×15 ml). The organic materials were combined, dried ($MgSO_4$), then concentrated under reduced pressure which gave 3.0 g of 3-(3-hydroxymethylphenyl)phenyl acetic acid.

3-(3-Hydroxymethylphenyl)phenyl acetic acid (3.0 g, 12.4 mmol), methanol (50 ml) and concentrated sulfuric acid (10 drops) were heated at reflux overnight in a 100 ml flask, quenched with saturated sodium bicarbonate solution, diluted with water (10 ml), extracted with methylene chloride (3×15 ml), washed with brine (1×15 ml), dried ($MgSO_4$), and concentrated under reduced pressure. The residue was purified by flash chromatography ($SiO_2$, 5:1 /hexane:ethyl acetate) which gave 0.90 g (30% from 3-bromophenyl acetic acid) of methyl 3-(3-hydroxymethylphenyl)phenyl acetate.
Part B:

Methyl 3-(3-hydroxymethylphenyl)phenyl acetate (0.87 g, 3.4 mmol) was dissolved in 1,2-dichloroethane (17 ml) in a dry 50 ml flask. D-Mannose pentaacetate (1.66 g, 4.24 mmol) was added in one portion, then borontrifluoride etherate (1.46 ml, 11.9 mmol) was added slowly. The mixture was stirred under nitrogen overnight at room temperature, then mixed with $H_2O$ (50 ml). The organic material was separated and the aqueous portion was extracted with methylene chloride (3×10 ml). The extracts were combined with the original organic fraction, dried ($MgSO_4$), then concentrated under reduced pressure. The residue was purified by flash chromatography ($SiO_2$, gradient elution hexane:ethyl acetate/3:1) which provided 1.50 g (75%) of methyl 3-(3-(2,3,4,6-tetra-O-acetyl-α-D-mannopyranosylmethyl) phenyl)phenyl acetate contaminated with a small amount of unreacted D-mannose pentaacetate which co-eluted with the product.

Part C:

Methyl 3-(3-(2,3,4,6-tetra-O-acetyl-α-D-mannopyranosylmethyl)phenyl)phenyl acetate (1.0 g, 1.7 mmol was dissolved in acetonitrile (10 ml) in a 50 ml flask, and treated with a solution of lithium hydroxide monohydrate (0.72 g, 17.0 mmol) in water (8 ml). The mixture was stirred at room temperature overnight then acidified to pH 3.5 with concentrated hydrochloric acid. The mixture was concentrated under reduced pressure and the residue was purified by HPLC (reverse phase C18, gradient elution 10–70% acetonitrile in water (0.1% trifluoroacetic acid), monitored at 254 nm) which gave 3-(3-(α-D-mannopyranosyloxymethyl)phenyl)phenylacetic acid (0.50 g, 73%); mp 74°–75° C.; $^1$H NMR: (300 MHz, DMSO-$d_6$) 7.20–7.60 (comp, 8H), 4.73 (d, 2H, J=12), 4.71 (s, 1H), 4.50 (d, 2H, J=12), 3.25–3.75 (comp, 11H plus water) ppm; IR (KBr): 3394, 2934, 1715, 1366, 1220, 1130, 1060 cm$^{-1}$; analysis: calculated for $C_{21}H_{24}O_9$, 0.15[$C_2HF_3O_2$]: 60.69 C, 5.77H; found: 60.60 C, 5.99% H.

Part D:

3-(3-(α-D-mannopyranosyloxymethyl)phenyl)phenylacetic acid (0.05 g, 0.12 mmol), methanol (10 ml), and concentrated sulfuric acid (2 drops) were heated reflux for 1 hour in a 25 ml flask, then quenched with saturated sodium bicarbonate solution, diluted with water (5 ml), extracted with methylene chloride (3×5 ml), washed with brine (10 ml), dried (MgSO$_4$), concentrated under reduced pressure. The residue was purified by flash chromatography (SiO$_2$, 5:1/methylene chloride:methanol) which gave methyl 3-(3-(α-D-mannopyranosyloxymethyl)phenyl)phenylacetate (0.04 g, 77%); $^1$H NMR: (300 MHz, DMSO-$d_6$) 7.2–7.6 (comp, 8H), 4.70 (s, 1H), 4.49–4.80 (comp, 7H), 3.75 (s, 2H), 3.62 (s, 3H), 3.30–3.50 (comp, 5H) ppm; IR: 3383, 1738, 1135, 1066 cm$^{-1}$.

EXAMPLE 18

Ethyl 3-(3-(2-α-D-mannopyranosyloxyphenyl)phenyl)propylphosphonate

Part A:

A solution of 2-(3-(2-α-D-mannopyranosyloxyphenyl)phenyl)ethanol (1.12 g, 2.46 mmol) in dichloromethane (15 ml) was added slowly to a suspension of Dess-Martin periodinane (4.95 g, 11.7 mmol) in dry dichloromethane (5 ml), and the reaction was stirred at room temperature overnight. The mixture was then diluted with ether and filtered; the filtrate was washed twice with saturated sodium bicarbonate solution and once with brine, then dried with magnesium sulfate. The solvent was removed in vacuo and the residue was purified by silica gel chromatography (4:1 hexane:ethyl acetate) to afford 2-(2-α-D-mannopyranosyloxyphenyl)phenylethanal (0.63 g, 57%).

Part B:

Tetraethylmethylenediphosphonate (0.37 g, 1.28 mmol) was dissolved in dry tetrahydrofuran (3.6 ml) under a blanket of nitrogen and the solution was cooled to −78° C. A 0.5M solution of potassium hexamethyldisilazide in toluene (2.56 ml, 1.28 mmol) was added dropwise, and the reaction was stirred for 10 minutes. A solution of 2-(2-α-D-mannopyranosyloxyphenyl)phenylethanal (0.58 g, 1.28 mmol) in tetrahydrofuran (3.8 ml) was then added, and the reaction was allowed to warm to room temperature as it stirred overnight. Water was then added and the mixture was extracted with ethyl acetate. The extracts were washed with water, 1N HCl, saturated sodium bicarbonate solution, brine, then dried over magnesium sulfate. The solvent was removed in vacuo and the residue was purified by silica gel chromatography (1:2 hexane:ethyl acetate) to afford diethyl 3-(3-(2-α-D-mannopyranosyloxyphenyl)phenyl)prop-1-enylphosphonate (0.46 g, 63%).

Part C:

Diethyl 3-(3-(2-α-D-mannopyranosyloxyphenyl)phenyl)prop-1-enylphosphonate (0.46 g, 0.80 mmol) was dissolved in ethanol (25 ml) and hydrogenated (40 psi H$_2$, 10% Pd/C) for 3 hours. The suspension was filtered through celite and the filtrate concentrated under reduced pressure to afford diethyl 3-(3-(2-α-D-mannopyranosyloxyphenyl)phenyl)propylphosphonate (0.46 g, quantitative).

Part D:

Diethyl 3-(3-(2-α-D-mannopyranosyloxyphenyl)phenyl)propylphosphonate (0.23 g, 0.40 mmol) was dissolved in methanol (2 ml). 2N Hydrochloric acid (0.5 ml) was added and the reaction was stirred overnight. The solution was brought to pH 10 by the addition of 2N NaOH and allowed to stir at room temperature for 3 hours. The reaction was heated at 60° C. for 18 hours, then at 80° C. for 116 hours. The solution was then cooled and acidified with 1N HCl, and the product was isolated by preparative reverse-phase HPLC on a Dynamax 300 Å 5 micron C18 column (21.4×250 mm) at a flow rate of 10 ml/min. An elution gradient of 0–50% solvent B over 20 minutes was used, with solvent B composed of 95% acetonitrile/water, 0.1% trifluoroacetic acid and solvent A composed of 5% acetonitrile/water, 0.1% trifluoroacetic acid. The effluent was monitored at 254 nm, and pure fractions were combined and lyophilized to yield (76.4 mg, 40%) of ethyl 3-(3-(2-α-D-mannopyranosyloxyphenyl)phenyl)propylphosphonate as a white solid, M.P.: 67°–70° C.; IR (KBr): 3404, 2931, 1478, 1454, 1423, 1222, 1108, 1043, 1008, 976, 797, 752, 706 cm$^{-1}$; NMR (300 MHz, D$_2$O): d 7.25 (m, 8H), 5.41 (s, 1H), 3.88 (m, 3H), 3.61 (m, 4H), 3.26 (m, 1H), 2.64 (m, 2H), 1.78 (m, 2H), 1.66 (m, 2H), 1.16 (t, 3H, J=6.9).

That which is claimed is:

1. A compound having the formula:

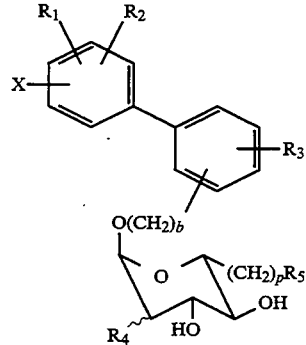

wherein X is selected from the group consisting of —(CH$_2$)$_n$CO$_2$H, —O(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_6$)CO$_2$H, (1-H-tetrazolyl-5-alkyl-), and —OH;

R$_1$ and R$_2$ are independently selected from the group consisting of hydrogen, alkyl, halogen, —OZ, —NO$_2$, —NH$_2$ and —NHZ;

R$_3$ is selected from the group consisting of hydrogen, halogen, alkyl, —OZ and —NHZ;

R$_4$ is selected from the group consisting of hydrogen, halogen, alkyl, hydroxyl, hydroxyl-O-sulfate and —OZ;

R$_5$ is selected from the group consisting of hydroxyl, —CN, —N$_3$, —NH$_2$, —NHNH$_2$, —NE$_1$E$_2$, —NHE$_1$, —NHCO(CH$_2$)$_n$CO$_2$H, —S(CH$_2$)$_m$CO$_2$H and —NHCHNHNH$_2$; and R$_6$ is selected from the group consisting of hydrogen, alkyl, aralkyl, hydroxyalkyl, aminoalkyl, alkyl carboxylic acid and alkyl carboxamide;

wherein n is 0 to 6, m is 1 to 6, p is 0 to 6, b is 0 to 2, Z is alkyl, aryl or aralkyl, D$_1$ and D$_2$ are independently hydrogen or alkyl, E$_1$ is alkyl or —(CH$_2$)$_8$CO$_2$H, and E$_2$ is alkyl, and the pharmaceutically acceptable salts, esters, and amides thereof.

2. The compound of claim 1 wherein X is —CH$_2$CO$_2$H; R$_1$, R$_2$ and R$_3$ are hydrogen; R$_4$ is —OH; R$_5$ is —SCH$_2$CO$_2$H; n is 1; b is 0; and the mannopyranoside moiety is attached to the R$_3$ containing phenyl ring in the ortho position.

3. The compound of claim 1 wherein X is —CH$_2$CO$_2$H; R$_1$, R$_2$ and R$_3$ are hydrogen; R$_4$ is —OH; R$_5$ is —N$_3$; n is 1; b is 0; and the mannopyranoside moiety is attached to the R$_3$ containing phenyl ring in the ortho position.

4. The compound of claim 1 wherein X is —CH$_2$CO$_2$H; R$_1$, R$_2$ and R$_3$ are hydrogen, R$_4$ and R$_5$ are —OH; n and b are 1; and the mannopyranoside moiety is attached to the R$_3$ containing phenyl ring in the meta position.

5. The compound of claim 1 wherein each alkyl substituent is lower alkyl.

6. A compound having the formula:

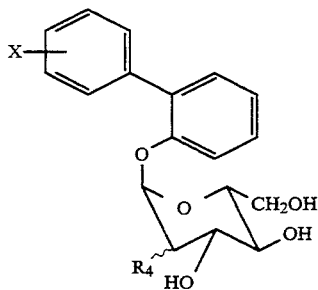

wherein X is —Q, (CH$_2$)$_n$Q, —O(CH$_2$)$_n$Q, —NH(CH$_2$)$_m$Q; —CONH(CH$_2$)$_n$Q, —(CH$_2$)$_n$O(CH$_2$)$_m$Q, —O(CH$_2$)$_n$O(CH$_2$)$_m$Q, or —CONH(CHR$_6$)Q;

R$_4$ is hydroxyl or hydrogen; R$_6$ is selected from the group consisting of hydrogen, alkyl, aralkyl, hydroxyalkyl, aminoalkyl, alkyl carboxylic acid and alkyl carboxamide, Q is —CO$_2$H, n is 0 to 6, and m is 1 to 6, and the pharmaceutically acceptable salts, esters, and amides thereof.

7. The compound of claim 6 wherein X is —CH$_2$CO$_2$H and R$_4$ is —OH.

8. The compound of claim 6 wherein X is —CO$_2$H and R$_4$ is —OH.

9. The compound of claim 6 wherein X is —CH$_2$OCH$_2$CO$_2$H and R$_4$ is —OH.

10. The compound of claim 6 wherein X is —CONHCH$_2$CO$_2$H and R$_4$ is —OH.

11. The compound of claim 6 wherein X is —OCH$_2$CO$_2$H and R$_4$ is —OH.

12. The compound of claim 6 wherein X is —CONHCH(CO$_2$H)(CH$_2$C$_6$H$_5$) and R$_4$ is —OH.

13. The compound of claim 6 wherein X is —CONHCH(CO$_2$H)(CH$_2$CH$_2$CO$_2$H) and R$_4$ is —OH.

14. The compound of claim 6 wherein X is —CO$_2$Li and R$_4$ is —OH.

15. The compound of claim 6 wherein X is —(CH$_2$)$_2$SO$_3$H and R$_4$ is —OH.

16. The compound of claim 6 wherein X is —CONHCH$_2$CH$_2$CO$_2$H and R$_4$ is —OH.

17. A method of inhibiting the binding of E-selectin and/or P-selectin to sialyl-Lewis$^x$ or sialyl-Lewis$^a$ presented on a cell surface comprising the step of administering to an animal in need of such treatment an amount of at least one compound having the formula:

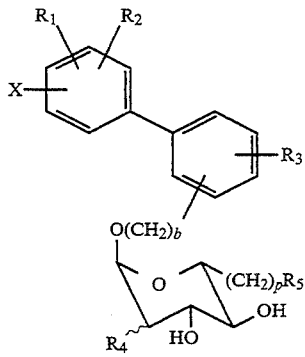

wherein said amount is effective for inhibition of said binding;

wherein X is selected from the group consisting of —(CH$_2$)$_n$CO$_2$H, —O(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_6$)CO$_2$H, and (1-H-tetrazolyl-5-alkyl-), and —OH;

R$_1$ and R$_2$ are independently selected from the group consisting of hydrogen, alkyl, halogen, —OZ, —NO$_2$, —NH$_2$ and —NHZ;

R$_3$ is selected from the group consisting of hydrogen, halogen, alkyl, —OZ and —NHZ;

R$_4$ is selected from the group consisting of hydrogen, halogen, alkyl, hydroxyl, hydroxyl-O-sulfate and —OZ;

R$_5$ is selected from the group consisting of hydrogen, hydroxyl, —CN, —N$_3$, —NH$_2$, —NHNH$_2$, —NE$_1$E$_2$, —NHE$_1$, —NHCO(CH$_2$)$_n$CO$_2$H, —S(CH$_2$)$_m$CO$_2$H and —NHCHNHNH$_2$; and R$_6$ is selected from the group consisting of hydrogen, alkyl, aralkyl, hydroxyalkyl, aminoalkyl, alkyl carboxylic acid and alkyl carboxamide;

wherein n is 0 to 6, m is 1 to 6, p is 0 to 6, b is 0 to 2, Z is alkyl, aryl or aralkyl, D$_1$ and D$_2$ are independently hydrogen or alkyl, E$_1$ is alkyl or —(CH$_2$)$_8$CO$_2$H, and E$_2$ is alkyl, and the pharmaceutically acceptable salts, esters, and amides thereof.

18. The method of claim 17 wherein each alkyl substituent is lower alkyl.

19. A pharmaceutically active composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 5,444,050  
DATED : August 22, 1995  
INVENTOR(S) : Kogan et al

Page 1 of 5

It is certified that error appears in the above-indentified patent and that said Letters Patent is hereby corrected as shown below:

Column 1, lines 33 through 63, delete

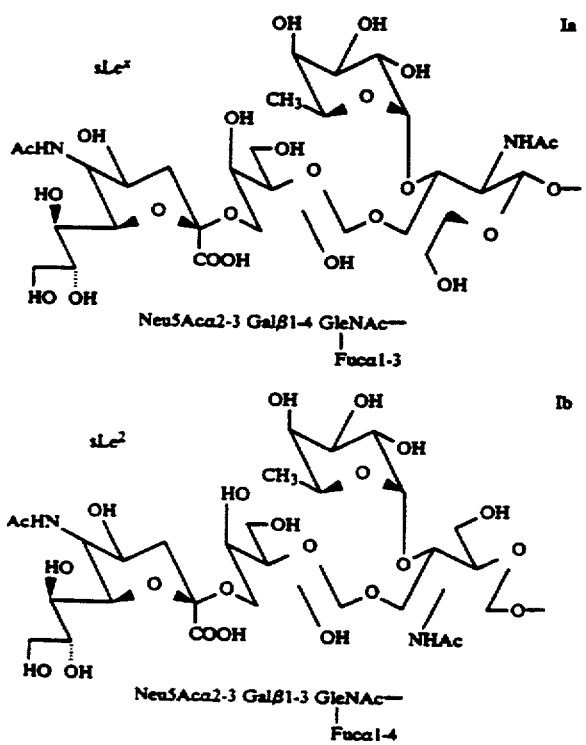

UNITED STATES PATENT AND TRADEMARK OFFICE
> # CERTIFICATE OF CORRECTION

PATENT NO. : 5,444,050
DATED : August 22, 1995
INVENTOR(S) : Kogan et al

It is certified that error appears in the above-indentified patent and that said Letters Patent is hereby corrected as shown below:

and insert

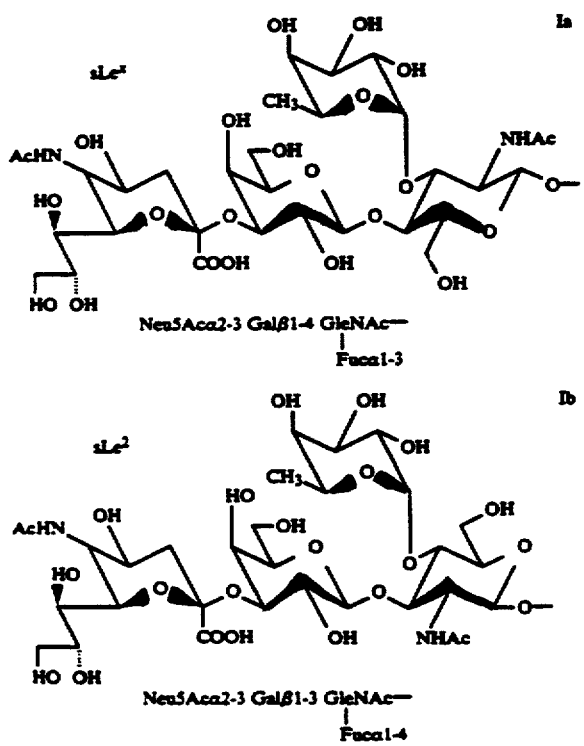

UNITED STATES PATENT AND TRADEMARK OFFICE
CERTIFICATE OF CORRECTION

PATENT NO. : 5,444,050
DATED : August 22, 1995
INVENTOR(S) : Kogan et al

It is certified that error appears in the above-indentified patent and that said Letters Patent is hereby corrected as shown below:

Column 12, lines 1 through 16, delete

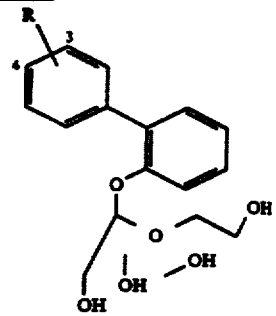

and insert

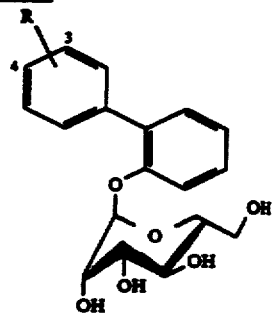

UNITED STATES PATENT AND TRADEMARK OFFICE
CERTIFICATE OF CORRECTION

PATENT NO.   : 5,444,050
DATED        : August 22, 1995
INVENTOR(S)  : Kogan et al It is certified that error appears in the above-indentified patent and that said Letters Patent is hereby corrected as shown below:

Column 3, line 24, delete [$-(CH_2)_n SO_2 H,$] and insert -- $-(CH_2)_n SO_3 H,$ --.

Column 12, line 20, delete [$-(CH_2)_n SO_2 H,$] and insert -- $-(CH_2)_n SO_3 H,$ --.

Column 25, line 46, delete [(3-(α-D-Mannopyranosyloxy)phenyl)phenyl] and insert --3-(2-(α-D-Mannopyranosyloxy)phenyl)phenyl--.

Column 26, line 43, after "falsk." insert -- α-D- --.

Column 29, line 63, delete [$^1$NMR:] and insert --$^1$H NMR:--.

Column 30, line 1, delete [$C_{20}H_{22}O_9 \cdot [H_2O]$ 1.1] and insert --$C_{20}H_{22}O_9 \cdot [H_2O].1.1$--.

UNITED STATES PATENT AND TRADEMARK OFFICE
CERTIFICATE OF CORRECTION

PATENT NO. : 5,444,050
DATED : August 22, 1995
INVENTOR(S) : Kogan et al

It is certified that error appears in the above-indentified patent and that said Letters Patent is hereby corrected as shown below:

Column 30, line 67, delete $[C_2HF_3O_2],]$ and insert $--[C_2HF_3O_2].--$.

Column 33, line 21, delete [4dime-] and insert --4-dime- --.

Column 33, line 31, delete [3-(2-(4-O-acetyl-2,3-O-isopropylidene-6-O-$\alpha$-] and insert --3-(2-(4-O-acetyl-2,3-O-isopropylidene-6-O-$\beta$- --.

Column 34, line 20, delete [(KBr:cm$^{-1}$] and insert --(KBr:cm$^{-1}$--.

Column 35, line 30, after ":" delete [6] and insert --$\sigma$--.

Column 36, line 18, delete [3-(2-(6(] and insert --3-(2-(6- --.

Column 39, line 24, delete $[C_{21}H_{24}O_9.0.15[C_2HF_3O_2]:]$ and insert $--C_{21}H_{24}O_8.0.15[C_2HF_3O_2]: --$.

Signed and Sealed this

Fifth Day of March, 1996

Attest:

BRUCE LEHMAN

*Attesting Officer*  Commissioner of Patents and Trademarks